US012586677B2

(12) United States Patent (10) Patent No.: US 12,586,677 B2
Tanaka et al. (45) Date of Patent: Mar. 24, 2026

(54) MANAGEMENT METHOD, MANAGEMENT SYSTEM, AND ELECTRONIC MEDICAL RECORD SYSTEM

(71) Applicant: NEC CORPORATION, Tokyo (JP)

(72) Inventors: Yuki Tanaka, Tokyo (JP); Kousuke Onoue, Tokyo (JP)

(73) Assignee: NEC CORPORATION, Tokyo (JP)

( * ) Notice: Subject to any disclaimer, the term of this patent is extended or adjusted under 35 U.S.C. 154(b) by 0 days.

(21) Appl. No.: 18/698,124

(22) PCT Filed: Oct. 4, 2022

(86) PCT No.: PCT/JP2022/037049
§ 371 (c)(1),
(2) Date: Apr. 3, 2024

(87) PCT Pub. No.: WO2023/058625
PCT Pub. Date: Apr. 13, 2023

(65) Prior Publication Data
US 2024/0412855 A1      Dec. 12, 2024

(30) Foreign Application Priority Data
Oct. 4, 2021 (JP) ................................. 2021-163406

(51) Int. Cl.
*G16H 40/20* (2018.01)
*G16H 10/40* (2018.01)
(Continued)

(52) U.S. Cl.
CPC ............. *G16H 40/20* (2018.01); *G16H 10/40* (2018.01); *G16H 10/60* (2018.01); *G16H 20/17* (2018.01)

(58) Field of Classification Search
CPC ........ G16H 10/40; G16H 40/20; G16H 80/00; G16H 10/60; G16H 20/17; G16H 20/10;
(Continued)

(56) References Cited

U.S. PATENT DOCUMENTS 9,507,917 B2    11/2016    Atlas et al.
2015/0278451 A1    10/2015    Kitano et al.
(Continued)

FOREIGN PATENT DOCUMENTS

JP        04-303720 A      10/1992
JP        2002-203040 A      7/2002
(Continued)

OTHER PUBLICATIONS

International Search Report for PCT/JP2022/037049, dated Dec. 20, 2022.
(Continued)

*Primary Examiner* — Igor N Borissov
(74) *Attorney, Agent, or Firm* — Sughrue Mion, PLLC

(57) ABSTRACT

A management method includes: a determination step in which the management system determines a predicted delivery date or a predicted required time when an administration item is delivered to a hospital by using an estimated time or an actual required time when an analysis institution analyzes a gene of a specimen of a patient, an estimated time or an actual required time when a creation institution creates a recipe of the administration item to a patient from a genetic analysis result, and/or an estimated time or an actual required time when a manufacturing institution manufactures the administration item according to the recipe; and a transmission step in which information for displaying the predicted delivery date or the predicted required time is transmitted to a terminal.

15 Claims, 14 Drawing Sheets

(51) Int. Cl.
 *G16H 10/60* (2018.01)
 *G16H 20/17* (2018.01)

(58) Field of Classification Search
 CPC ........ G06N 20/00; G06Q 10/08; G06Q 50/04;
 G16B 20/20
 USPC ............................................................. 705/3
 See application file for complete search history.

(56) References Cited

U.S. PATENT DOCUMENTS

| | | | |
|---|---|---|---|
| 2018/0250399 A1 | 9/2018 | Lisziewicz et al. | |
| 2020/0268860 A1* | 8/2020 | Susarchick | A61K 39/12 |
| 2022/0129473 A1 | 4/2022 | Inomata et al. | |
| 2022/0215457 A1 | 7/2022 | Akabori et al. | |
| 2024/0291660 A1* | 8/2024 | Mahmood | G16H 20/00 |

FOREIGN PATENT DOCUMENTS

| | | |
|---|---|---|
| JP | 2003-308367 A | 10/2003 |
| JP | 2010-170480 A | 8/2010 |
| JP | 2014-095931 A | 5/2014 |
| JP | 2020-510698 A | 4/2020 |
| JP | 2020-119207 A | 8/2020 |
| JP | 2020-537635 A | 12/2020 |
| JP | 2021-056972 A | 4/2021 |
| TW | 200514848 A | 10/2003 |
| WO | 2005/040387 A1 | 5/2005 |
| WO | 2020/113098 A1 | 6/2020 |

OTHER PUBLICATIONS

Japanese Office Action dated Sep. 16, 2025 in Application No. 2023-552882.
Office Action issued Oct. 4, 2024 in Taiwanese Application No. 111137482.
Extended European Search Report dated Dec. 17, 2024 from the European Patent Office in Application No. 22878494.8.
Özlem Türeci et al., "Challenges towards the realization of individualized cancer vaccines", Nature Biomedical Engineering, 2018, vol. 2, No. 8, Jul. 2018, pp. 566-569 (4 pages total).

* cited by examiner

5

56

PROCESSOR

561
DELIVERY DATE
MANAGEMENT MEANS

562
COMMUNICATION
CONTROL MEANS

563
ID MANAGEMENT
MEANS

564
PIPELINE
MANAGEMENT MEANS

565
GENOME INFORMATION
MANAGEMENT MEANS

566
QUALITY INFORMATION
MANAGEMENT MEANS

567
ACCESS CONTROL
MEANS

568
BLOCKCHAIN
PROCESSING MEANS

51 — INPUT INTERFACE

STORAGE — 53

MEMORY — 54

52 — COMMUNICATION
MODULE

OUTPUT INTERFACE — 55

FIG. 3

T5: TABLE OF MANAGEMENT SYSTEM

| HOSPITAL ID | PATIENT ID | SPECIMEN ID | COMMON ID | SEQUENCE FILE NAME | RECIPE ID | RECIPE FILE NAME | VACCINE ID |
|---|---|---|---|---|---|---|---|
| H1 | 1 | xxxx-yyy-N (NORMAL TISSUE), xxxx-yyy-T (CANCER TISSUE) | C001 | xxxx_nDNA (NORMAL DNA), xxxx_tDNA (CANCER DNA), xxxx_tRNA (CANCER RNA) | R001 | yyyy | V001 |

T1: TABLE OF HOSPITAL SYSTEM

| PATIENT ID | SPECIMEN ID | VACCINE ID |
|---|---|---|
| 1 | xxxx-yyy-N (NORMAL TISSUE), xxxx-yyy-T (CANCER TISSUE) | V001 |

T2: TABLE OF GENETIC ANALYSIS INSTITUTION SYSTEM

| SPECIMEN ID | SEQUENCE FILE NAME |
|---|---|
| xxxx-yyy-N (NORMAL TISSUE), xxxx-yyy-T (CANCER TISSUE) | xxxx_nDNA (NORMAL DNA), xxxx_tDNA (CANCER DNA), xxxx_tRNA (CANCER RNA) |

T3: TABLE OF RECIPE CREATION INSTITUTION SYSTEM

| SEQUENCE FILE NAME | RECIPE ID | RECIPE FILE NAME |
|---|---|---|
| xxxx_nDNA (NORMAL DNA), xxxx_tDNA (CANCER DNA), xxxx_tRNA (CANCER RNA) | R001 | yyyy |

T4: TABLE OF VACCINE MANUFACTURING INSTITUTION SYSTEM

| RECIPE FILE NAME | VACCINE ID |
|---|---|
| yyyy | V001 |

Figure 6:
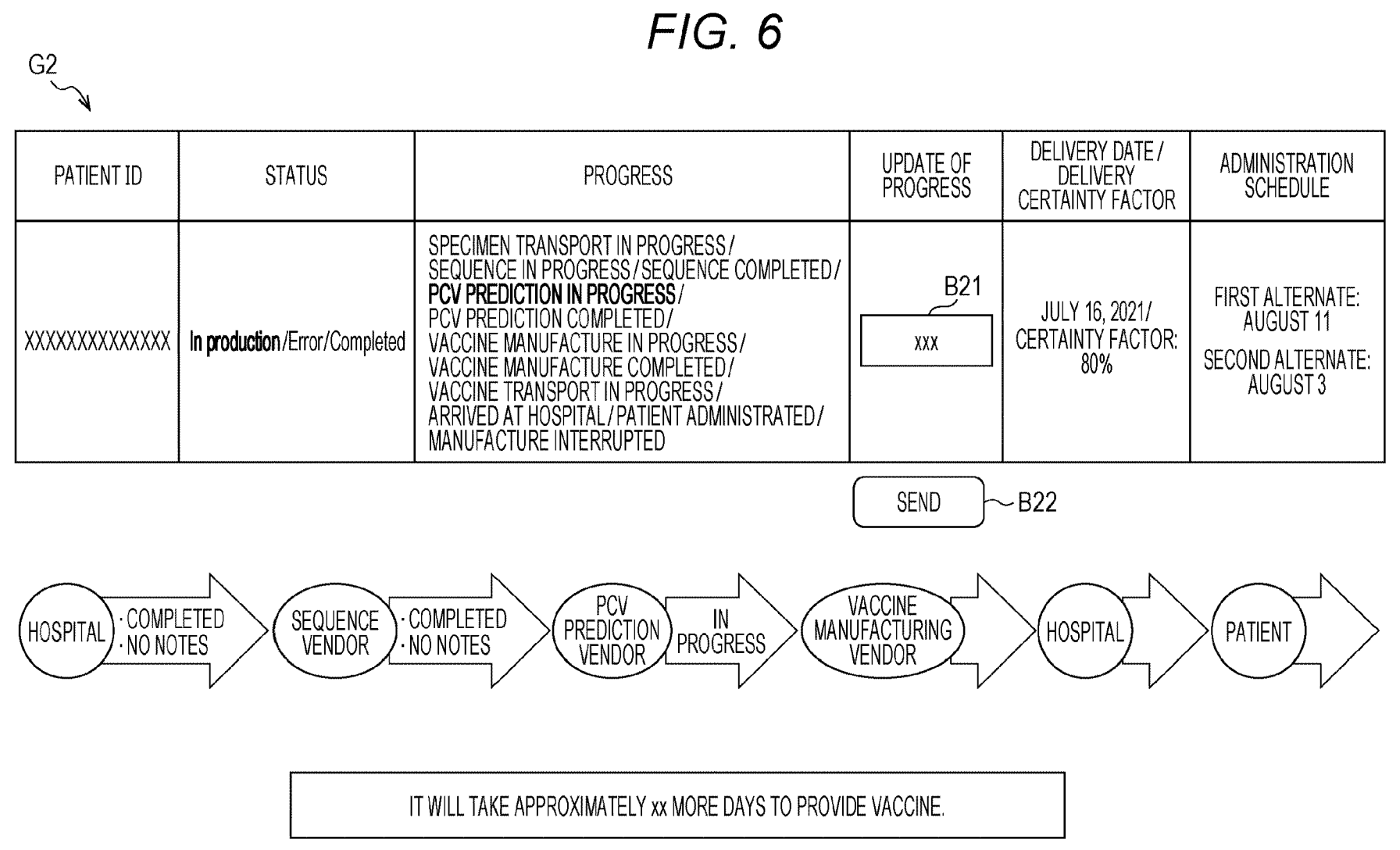

| PATIENT ID | STATUS | PROGRESS | UPDATE OF PROGRESS | DELIVERY DATE/ DELIVERY CERTAINTY FACTOR | ADMINISTRATION SCHEDULE |
|---|---|---|---|---|---|
| XXXXXXXXXXXXXX | In production/Error/Completed | SPECIMEN TRANSPORT IN PROGRESS/ SEQUENCE IN PROGRESS/SEQUENCE COMPLETED/ PCV PREDICTION IN PROGRESS/ PCV PREDICTION COMPLETED/ VACCINE MANUFACTURE IN PROGRESS/ VACCINE MANUFACTURE COMPLETED/ VACCINE TRANSPORT IN PROGRESS/ ARRIVED AT HOSPITAL/PATIENT ADMINISTRATED/ MANUFACTURE INTERRUPTED | B21 \ xxx | JULY 16, 2021/ CERTAINTY FACTOR: 80% | FIRST ALTERNATE: AUGUST 11 SECOND ALTERNATE: AUGUST 3 |

SEND — B22

HOSPITAL
· COMPLETED
· NO NOTES

SEQUENCE VENDOR
· COMPLETED
· NO NOTES

PCV PREDICTION VENDOR
IN PROGRESS

VACCINE MANUFACTURING VENDOR

HOSPITAL

PATIENT

IT WILL TAKE APPROXIMATELY xx MORE DAYS TO PROVIDE VACCINE.

Figure 7:
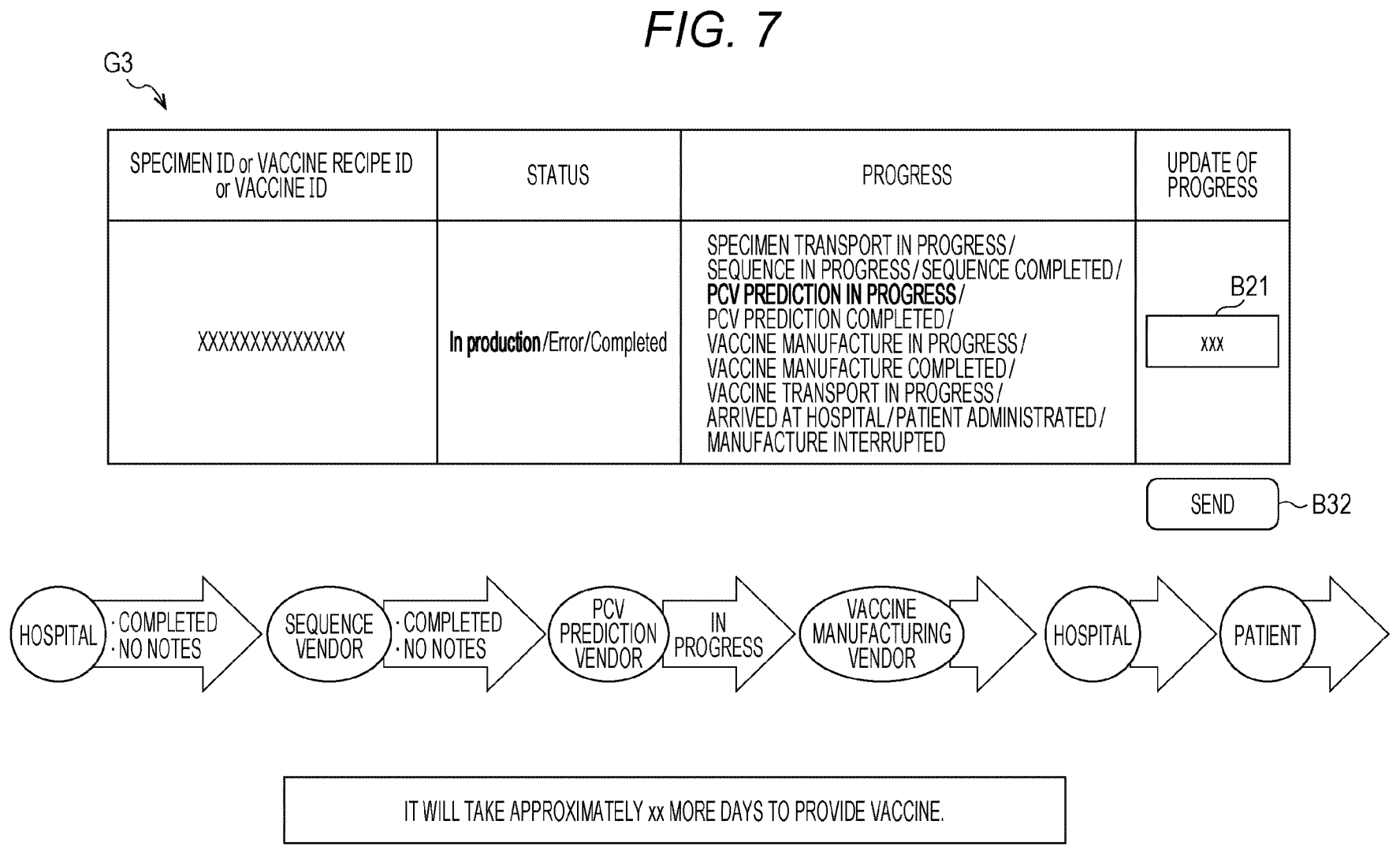

| SPECIMEN ID or VACCINE RECIPE ID or VACCINE ID | STATUS | PROGRESS | UPDATE OF PROGRESS |
|---|---|---|---|
| XXXXXXXXXXXXXX | In production/Error/Completed | SPECIMEN TRANSPORT IN PROGRESS/ SEQUENCE IN PROGRESS/SEQUENCE COMPLETED/ PCV PREDICTION IN PROGRESS/ PCV PREDICTION COMPLETED/ VACCINE MANUFACTURE IN PROGRESS/ VACCINE MANUFACTURE COMPLETED/ VACCINE TRANSPORT IN PROGRESS/ ARRIVED AT HOSPITAL/PATIENT ADMINISTRATED/ MANUFACTURE INTERRUPTED | B21 / xxx |

B32 — SEND

HOSPITAL
· COMPLETED
· NO NOTES

SEQUENCE VENDOR
· COMPLETED
· NO NOTES

PCV PREDICTION VENDOR
IN PROGRESS

VACCINE MANUFACTURING VENDOR

HOSPITAL

PATIENT

IT WILL TAKE APPROXIMATELY xx MORE DAYS TO PROVIDE VACCINE.

FIG. 8

| DATA/ORGANIZATION | HOSPITAL | GENETIC ANALYSIS INSTITUTION | RECIPE CREATION INSTITUTION | VACCINE MANUFACTURING INSTITUTION | ADMINISTRATOR | LABORATORY/VENDOR |
|---|---|---|---|---|---|---|
| COMMON ID | × (AVAILABLE ONLY IN MODIFICATION 1) | × (AVAILABLE ONLY IN MODIFICATION 1) | × (AVAILABLE ONLY IN MODIFICATION 1) | × (AVAILABLE ONLY IN MODIFICATION 1) | ○ | × (AVAILABLE ONLY IN MODIFICATION 1) |
| SEQUENCE DATA | × | ○ NOTE THAT ONLY WHEN IT CAN BE DETERMINED THAT ACCESS IS FROM DOMESTIC CENTER IDENTICAL TO THAT OF PATIENT OF SEQUENCE DATA. | ○ NOTE THAT ONLY WHEN IT CAN BE DETERMINED THAT ACCESS IS FROM DOMESTIC CENTER IDENTICAL TO THAT OF PATIENT OF SEQUENCE DATA. | × | × | × |
| CLINICAL DATA | ○ NOTE THAT ONLY WHEN IT CAN BE DETERMINED THAT ACCESS IS FROM DOMESTIC CENTER IDENTICAL TO THAT OF PATIENT OF SEQUENCE DATA. | × | △ (IN PRINCIPLE, BROWSING IS NOT PERMITTED, BUT WITH CONSENT OF PATIENT, BROWSING IS PERMITTED IF USED FOR IMPROVING ACCURACY OF PREDICTION SYSTEM.) | × | × | × |
| SEQUENCE REPORT | ○ NOTE THAT ONLY WHEN IT CAN BE DETERMINED THAT ACCESS IS FROM DOMESTIC CENTER IDENTICAL TO THAT OF PATIENT OF SEQUENCE DATA. | ○ NOTE THAT ONLY WHEN IT CAN BE DETERMINED THAT ACCESS IS FROM DOMESTIC CENTER IDENTICAL TO THAT OF PATIENT OF SEQUENCE DATA. | △ (IN PRINCIPLE, BROWSING IS NOT PERMITTED, BUT WITH CONSENT OF PATIENT, BROWSING IS PERMITTED IF USED FOR IMPROVING ACCURACY OF PREDICTION SYSTEM.) | × | × | × |
| QC DATA | ○ NOTE THAT ONLY WHEN IT CAN BE DETERMINED THAT ACCESS IS FROM DOMESTIC CENTER IDENTICAL TO THAT OF PATIENT OF SEQUENCE DATA. | × | ○ NOTE THAT ONLY WHEN IT CAN BE DETERMINED THAT ACCESS IS FROM DOMESTIC CENTER IDENTICAL TO THAT OF PATIENT OF SEQUENCE DATA. | × | × | × |
| VACCINE MANUFACTURING QUALITY DATA | ○ NOTE THAT ONLY WHEN IT CAN BE DETERMINED THAT ACCESS IS FROM DOMESTIC CENTER IDENTICAL TO THAT OF PATIENT OF SEQUENCE DATA. | × | △ (IN PRINCIPLE, BROWSING IS NOT PERMITTED, BUT WITH CONSENT OF PATIENT, BROWSING IS PERMITTED IF USED FOR IMPROVING ACCURACY OF PREDICTION SYSTEM.) | ○ NOTE THAT ONLY WHEN IT CAN BE DETERMINED THAT ACCESS IS FROM DOMESTIC CENTER IDENTICAL TO THAT OF PATIENT OF SEQUENCE DATA. | × | × |
| LABORATORY DATA | ○ NOTE THAT ONLY WHEN IT CAN BE DETERMINED THAT ACCESS IS FROM DOMESTIC CENTER IDENTICAL TO THAT OF PATIENT OF SEQUENCE DATA. | × | △ (IN PRINCIPLE, BROWSING IS NOT PERMITTED, BUT WITH CONSENT OF PATIENT, BROWSING IS PERMITTED IF USED FOR IMPROVING ACCURACY OF PREDICTION SYSTEM.) | × | × | ○ NOTE THAT ONLY WHEN IT CAN BE DETERMINED THAT ACCESS IS FROM DOMESTIC CENTER IDENTICAL TO THAT OF PATIENT OF SEQUENCE DATA. |
| MONITORING DATA AFTER ADMINISTRATION | ○ NOTE THAT ONLY WHEN IT CAN BE DETERMINED THAT ACCESS IS FROM DOMESTIC CENTER IDENTICAL TO THAT OF PATIENT OF SEQUENCE DATA. | × | △ (IN PRINCIPLE, BROWSING IS NOT PERMITTED, BUT WITH CONSENT OF PATIENT, BROWSING IS PERMITTED IF USED FOR IMPROVING ACCURACY OF PREDICTION SYSTEM.) | × | × | × |
| SYSTEM LOG | × | × | × | × | ○ | × |

FIG. 9

PATIENT ID [ xxxxxxxxx ]    B41

SEND    B42

G4

SEARCH RESULTS BY PATIENT ID xxxxxxxxxx ARE AS FOLLOWS.

| PATIENT ID | STATUS | PROGRESS | SEQUENCE REPORT | QC DATA | VACCINE MANUFACTURING QUALITY DATA | LABORATORY DATA | CLINICAL DATA BEFORE (ADMINISTRATION) | MONITORING DATA |
|---|---|---|---|---|---|---|---|---|
| XXXXX XXXXX XXXX | In production | SEQUENCE IN PROGRESS | https://xxx | https://xxx | https://xxx | https://xxx | https://xxx | https://xxx |
| XXXXX XXXXX XXXX | Completed | PATIENT ADMINISTRATED | https://xxx | https://xxx | https://xxx | https://xxx | https://xxx | https://xxx |
| XXXXX XXXXX XXXX | Completed | PATIENT ADMINISTRATED | https://xxx | https://xxx | https://xxx | https://xxx | https://xxx | https://xxx |
| XXXXX XXXXX XXXX | Completed | PATIENT ADMINISTRATED | https://xxx | https://xxx | https://xxx | https://xxx | https://xxx | https://xxx |
| XXXXX XXXXX XXXX | CANNOT BE BROWSED DUE TO LACK OF AUTHORITY. | CANNOT BE BROWSED DUE TO LACK OF AUTHORITY. | CANNOT BE BROWSED DUE TO LACK OF AUTHORITY. | CANNOT BE BROWSED DUE TO LACK OF AUTHORITY. | CANNOT BE BROWSED DUE TO LACK OF AUTHORITY. | CANNOT BE BROWSED DUE TO LACK OF AUTHORITY. | CANNOT BE BROWSED DUE TO LACK OF AUTHORITY. | CANNOT BE BROWSED DUE TO LACK OF AUTHORITY. |
| XXXXX XXXXX XXXX | CANNOT BE BROWSED DUE TO LACK OF AUTHORITY. | CANNOT BE BROWSED DUE TO LACK OF AUTHORITY. | CANNOT BE BROWSED DUE TO LACK OF AUTHORITY. | CANNOT BE BROWSED DUE TO LACK OF AUTHORITY. | CANNOT BE BROWSED DUE TO LACK OF AUTHORITY. | CANNOT BE BROWSED DUE TO LACK OF AUTHORITY. | CANNOT BE BROWSED DUE TO LACK OF AUTHORITY. | CANNOT BE BROWSED DUE TO LACK OF AUTHORITY. |
| CANNOT BE BROWSED DUE TO LACK OF AUTHORITY. | | | | | | | | |

FIG. 10

T5b: TABLE OF MANAGEMENT SYSTEM

| HOSPITAL ID | PATIENT ID | SPECIMEN ID | COMMON ID | SEQUENCE FILE NAME | RECIPE FILE NAME |
|---|---|---|---|---|---|
| H1 | 1 | xxxx-yyy-N (NORMAL TISSUE), xxxx-yyy-T (CANCER TISSUE) | C001 | xxxx_nDNA (NORMAL DNA), xxxx_tDNA (CANCER DNA), xxxx_tRNA (CANCER RNA) | yyyy |

T1b: TABLE OF HOSPITAL SYSTEM

| PATIENT ID | SPECIMEN ID | COMMON ID |
|---|---|---|
| 1 | xxxx-yyy-N (NORMAL TISSUE), xxxx-yyy-T (CANCER TISSUE) | C001 |

T2b: TABLE OF GENETIC ANALYSIS INSTITUTION SYSTEM

| SPECIMEN ID | COMMON ID | SEQUENCE FILE NAME |
|---|---|---|
| xxxx-yyy-N (NORMAL TISSUE), xxxx-yyy-T (CANCER TISSUE) | C001 | xxxx_nDNA (NORMAL DNA), xxxx_tDNA (CANCER DNA), xxxx_tRNA (CANCER RNA) |

T3b: TABLE OF RECIPE CREATION INSTITUTION SYSTEM

| SEQUENCE FILE NAME | COMMON ID | RECIPE FILE NAME |
|---|---|---|
| xxxx_nDNA (NORMAL DNA), xxxx_tDNA (CANCER DNA), xxxx_tRNA (CANCER RNA) | C001 | yyyy |

T4b: TABLE OF VACCINE MANUFACTURING INSTITUTION SYSTEM

| COMMON ID | RECIPE FILE NAME |
|---|---|
| C001 | yyyy |

T5c: TABLE OF MANAGEMENT SYSTEM

| HOSPITAL ID | SPECIMEN ID | SEQUENCE FILE NAME | COMMON ID | RECIPE ID | RECIPE FILE NAME | VACCINE ID |
|---|---|---|---|---|---|---|
| H1 | xxxx–yyy–N (NORMAL TISSUE), xxxx–yyy–T (CANCER TISSUE) | xxxx_nDNA (NORMAL DNA), xxxx_tDNA (CANCER DNA), xxxx_tRNA (CANCER RNA) | C001 | R001 | yyyy | V001 |

T2c: TABLE OF GENETIC ANALYSIS INSTITUTION SYSTEM

| HOSPITAL ID | SPECIMEN ID | SEQUENCE FILE NAME |
|---|---|---|
| H1 | xxxx–yyy–N (NORMAL TISSUE), xxxx–yyy–T (CANCER TISSUE) | xxxx_nDNA (NORMAL DNA), xxxx_tDNA (CANCER DNA), xxxx_tRNA (CANCER RNA) |

T4c: TABLE OF VACCINE MANUFACTURING INSTITUTION SYSTEM

| RECIPE FILE NAME | VACCINE ID |
|---|---|
| yyyy | V001 |

T1c: TABLE OF HOSPITAL SYSTEM

| PATIENT ID | SPECIMEN ID | VACCINE ID |
|---|---|---|
| 1 | xxxx–yyy–N (NORMAL TISSUE), xxxx–yyy–T (CANCER TISSUE) | V001 |

T3c: TABLE OF RECIPE CREATION INSTITUTION SYSTEM

| SEQUENCE FILE NAME | RECIPE ID | RECIPE FILE NAME |
|---|---|---|
| xxxx_nDNA (NORMAL DNA), xxxx_tDNA (CANCER DNA), xxxx_tRNA (CANCER RNA) | R001 | yyyy |

MANAGEMENT METHOD, MANAGEMENT SYSTEM, AND ELECTRONIC MEDICAL RECORD SYSTEM

CROSS REFERENCE TO RELATED APPLICATIONS

This application is a National Stage of International Application No. PCT/JP2022/037049 filed Oct. 4, 2022, claiming priority based on Japanese Patent Application No. 2021-163406 filed Oct. 4, 2021.

TECHNICAL FIELD

The present invention relates to a management method, a management system, and an electronic medical record system.

BACKGROUND ART

In cancer medicine so far, treatments and drugs have been selected for each type of cancer such as lung cancer, colorectal cancer, and breast cancer. However, in the 2000s, elucidation of molecules (proteins) that cause cancer and genetic mutations that are bases of the cancer has progressed, and "molecularly targeted drugs" acting on such molecules, genes, and the like can be used for therapy. Further developed from molecular target drugs, therapies targeting individual molecules and genetic mutations of patients are also developed. Here, performing a treatment suitable for each person according to not only the type of cancer but also characteristics of cancer such as genetic mutation is referred to as "personalized treatment". Conventionally, "personalized treatment" based on cancer gene information has been performed mainly on the basis of "cancer gene examination" for examining a small number of genes and "cancer gene panel examination" for examining a large number of genes simultaneously.

In recent years, a treatment (hereinafter, referred to as cancer vaccine treatment) using cancer immunotherapy called "attack and eliminate cancer cells by the action of the immune system inherent in humans" has further progressed. A "peptide vaccine" is known as one of cancer vaccine treatments. The peptide vaccine contains an antigen that is a marker of cancer. When a peptide containing the antigen is directly injected into a body, an immune function originally possessed by a human senses the abnormality and targets the antigen that is the marker of cancer to attack and kill cancer cells.

In recent years, it has become an era in which genetic mutations of cancers of respective patients can be comprehensively and simply known, and the importance of "peptides" newly generated by the genetic mutations has been highlighted in cancer immunotherapy. Such a peptide is a mutated peptide called "neoantigen". It has been revealed that when they get on human leukocyte antigen (HLA) and come out on the surface of cancer cells, cytotoxic T lymphocytes (CTLs) regard them as an enemy and can kill the cancer cells because they are peptides not on the surface of normal cells. Currently, clinical trials are being conducted in Europe and the United States to confirm whether individualized cancer vaccine therapy using "neoantigens" is effective as a cancer treatment method or a recurrence prevention method. In addition, Patent Literature 1 discloses a method for identifying a fragment of a polypeptide that is immunogenic to a specific human subject and a method for preparing an individualized pharmaceutical composition containing the polypeptide fragment.

CITATION LIST

Patent Literature

Patent Literature 1: JP 2020-510698 A

SUMMARY OF INVENTION

Technical Problem

Since the type and number of mutated peptides called "neoantigens" vary depending on the individual patient, there is a need to produce a peptide vaccine from genetic mutations of cancer tissues of patients individually for each patient. Here, in a case of personalized medicine (for example, personalized cancer vaccine therapy), there are a step in which a genetic analysis institution (for example, sequence vendor) analyzes a gene of a specimen of a patient, a step in which a recipe creation institution creates a recipe of an administration item (for example, vaccine) to the patient from a result of the genetic analysis, and a step in which a vaccine manufacturing institution manufactures an administration item (for example, vaccine) according to the recipe.

As described above, it is assumed that there are a plurality of steps in vaccine production and an external vendor is utilized for a part or most of the steps, and therefore there is a high possibility that the vaccine is produced on order. Therefore, there is a problem that it is difficult to grasp the delivery date of the administration item (for example, vaccine) to be administered to a patient.

In addition to the cancer vaccine, autoimmune diseases also have similar treatment possibilities, and a similar problem exists in personalized medicine for autoimmune diseases.

The present invention has been made in view of the above problems, and an object of the present invention is to provide a management method, a management system, and an electronic medical record system that enable grasping of a delivery date of an administration item for personalized medicine.

Solution to Problem

A management method according to a first aspect of the present invention includes: a determination step in which the management system determines a predicted delivery date or a predicted required time when an administration item is delivered to a hospital by using an estimated time or an actual required time when an analysis institution analyzes a gene of a specimen of a patient, an estimated time or an actual required time when a creation institution creates a recipe of the administration item to a patient from a genetic analysis result, and/or an estimated time or an actual required time when a manufacturing institution manufactures the administration item according to the recipe; and a transmission step in which information for displaying the predicted delivery date or the predicted required time is transmitted to a terminal.

A management method according to a second aspect of the present invention is the management method according to the first aspect, the management method including: a plurality of candidates for the analysis institution and/or a plurality of candidates for the creation institution and/or a plurality of candidates for the manufacturing institution, in which a predicted delivery date or a predicted required time when the administration item is delivered to a hospital is determined in the determination step according to an analysis institution of an order destination and/or a creation institution of an order destination and/or a manufacturing institution of an order destination.

A management method according to a third aspect of the present invention is the management method according to the first or second aspect, and includes a step of, in a case where a request for a progress status of the administration item is received from a terminal, replying in which the management system replies information for displaying the progress status to the terminal.

A management method according to a fourth aspect of the present invention is the management method according to the third aspect, in which a browsing authority is assigned to each institution and stored in a storage device, the management method further including, in the step of replying, a step of replying a progress status within a range permitted by a browsing authority assigned to an institution to which a terminal that has requested the progress status belongs.

A management method according to a fifth aspect of the present invention is the management method according to any one of the first to fourth aspects, and includes a step of, in a case where the predicted delivery date or the predicted required time is delayed, notifying a doctor terminal logged in to a service provided by the management system by a doctor in charge of the patient or a doctor in charge of the patient.

A management method according to a sixth aspect of the present invention is the management method according to any one of the first to fifth aspects, and includes a step of allowing a reception of setting an administration schedule to the patient when a certainty factor of a delivery date exceeds a reference.

A management method according to a seventh aspect of the present invention is the management method according to any one of the first to sixth aspects, and includes: a step in which the management system transmits a gene sequence data to a system of the creation institution in a case where the gene sequence data is received from the analysis institution; and a step in which the management system transmits a recipe to a system of the manufacturing institution in a case where the recipe is received from the creation institution.

A management method according to an eighth aspect of the present invention is the management method according to any one of the first to seventh aspects, and includes a step of, in a case where the management system receives quality information on a specimen, quality information on a gene sequence, quality information on a recipe, and/or quality information on a vaccine from a hospital system, an analysis institution system, a creation institution system, and/or a manufacturing institution system, storing the information received in a storage device.

A management method according to a ninth aspect of the present invention is the management method according to the eighth aspect, in which the administration item is a vaccine, and the recipe is peptide sequence data of neoantigens, data of proteins, or aggregate data of administered compounds.

A management method according to a tenth aspect of the present invention is the management method according to any one of the first to ninth aspects, and includes a step of writing an update history and/or update data of the storage device in a blockchain.

A management method according to an eleventh aspect of the present invention is the management method according to any of the first to tenth aspects, and includes a step of, according to a gene fragment amount obtained from a specimen and/or a base amount of a gene to be read, determining an estimated time for analyzing the gene.

A management method according to a twelfth aspect of the present invention is the management method according to any one of the first to eleventh aspects, and includes a step of, according to a sequence data amount obtained as a result of genetic analysis, determining an estimated time for creating the recipe.

A management method according to a thirteenth aspect of the present invention is the management method according to any one of the first to eleventh aspects, and includes a step of, according to a genetic mutation amount, determining an estimated time for creating the recipe.

A management method according to a fourteenth aspect of the present invention is the management method according to any one of the first to eleventh aspects, and includes a step of, according to a name of an organ from which a specimen is obtained, determining an estimated time for creating the recipe.

A management method according to a fifteenth aspect of the present invention is the management method according to any one of the first to eleventh aspects, and determines an estimated time for creating the recipe by inputting at least one of a gene fragment amount and/or a base amount of a gene to be read, a sequence data amount, and a genetic mutation amount to a machine learning model trained using learning data in which at least one of a gene fragment amount and a base amount of a gene to be read, a sequence data amount, and a genetic mutation amount is input and an estimated delivery date is output.

A management method according to a sixteenth aspect of the present invention is the management method according to any one of the first to fifteenth aspects, and further includes an access control step of restricting information that can be accessed by each institution.

A management system according to a seventeenth aspect of the present invention includes: a delivery date management means that determines a predicted delivery date or a predicted required time when an administration item is delivered to a hospital by using an estimated time or an actual required time when an analysis institution analyzes a gene of a specimen of a patient, an estimated time or an actual required time when a creation institution creates a recipe of the administration item to a patient from a genetic analysis result, and an estimated time or an actual required time when a manufacturing institution manufactures the administration item according to the recipe; and a communication control means that transmits information for displaying the predicted delivery date or the predicted required time to a terminal.

An electronic medical record system according to an eighteenth aspect of the present invention includes the management system according to the seventeenth aspect of the present invention.

Advantageous Effects of Invention

According to one aspect of the present invention, information for displaying the predicted delivery date or the predicted required time of the administration item for personalized medicine is displayed on the terminal, so that the delivery date of the administration item for personalized medicine can be grasped.

BRIEF DESCRIPTION OF DRAWINGS

FIG. 3 is a diagram illustrating a schematic configuration of a database of each system in the present embodiment.

FIG. 6 is an example of a progress management screen displayed on the hospital terminal.

FIG. 7 is an example of a progress management screen displayed on an analyst terminal, a creator terminal, or a manufacturer terminal.

FIG. 8 is an example of a list of access restrictions on data to be accessed.

FIG. 9 is an example of a search result screen displayed on the hospital terminal.

FIG. 10 is a diagram illustrating a schematic configuration of a database of each system in Modification 1.

FIG. 11 is an example of a sequence diagram according to Modification 1.

FIG. 12 is a diagram illustrating a schematic configuration of a database of each system in Modification 2.

DESCRIPTION OF EMBODIMENTS

Figure 1:
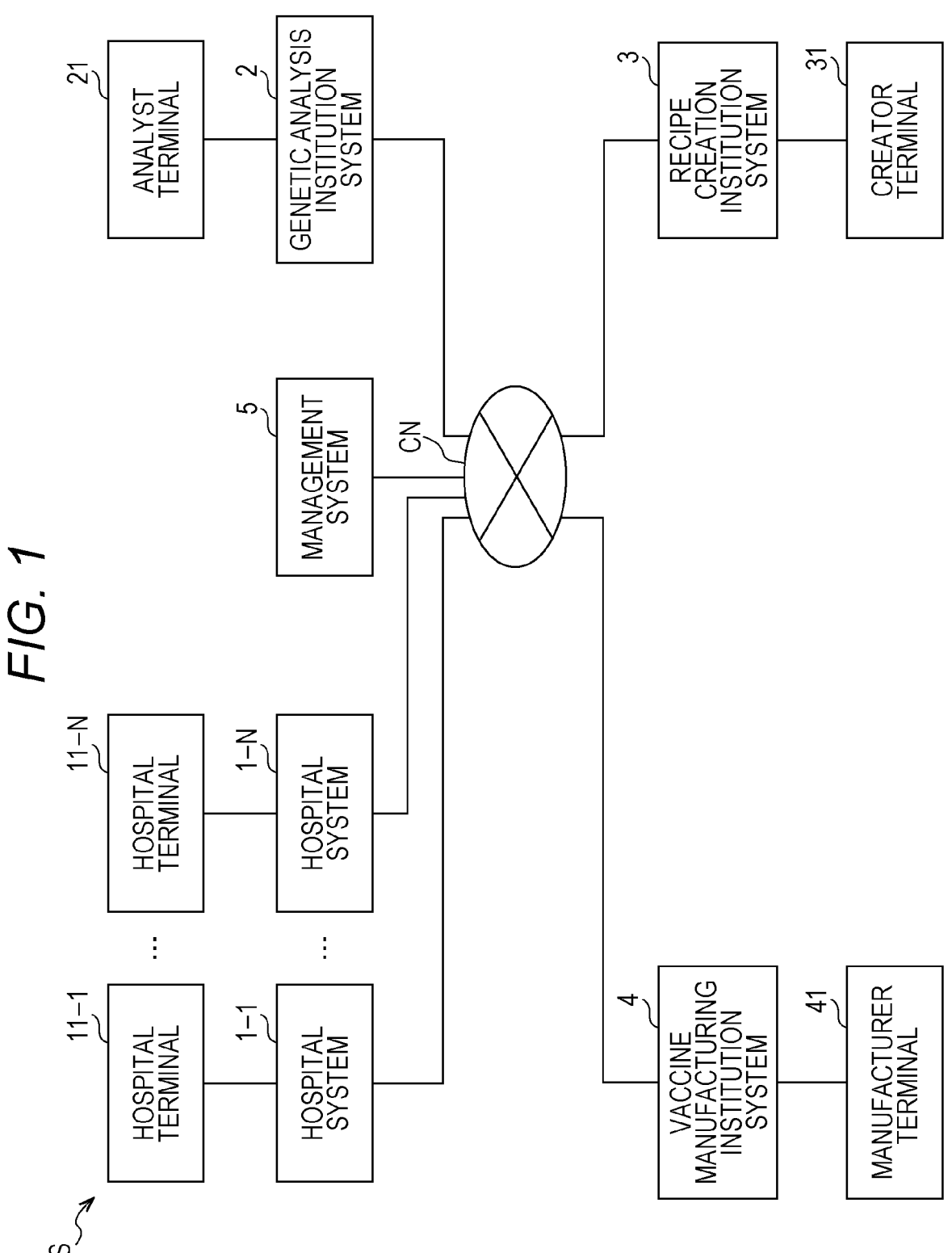
FIG. 1 is a schematic block diagram of an information processing system according to the present embodiment.

Hereinafter, each embodiment will be described with reference to the drawings. However, unnecessarily detailed description may be omitted. For example, a detailed description of a well-known matter and a repeated description of substantially the same configuration may be omitted. This is to avoid unnecessary redundancy of the following description and to facilitate understanding of those skilled in the art.

Problems to be Solved by Present Embodiment

In normal distribution of pharmaceuticals, there is no need to associate with patient information for mass production. In a case of an oncogene panel test, patient data is closed in a hospital or in a genome sequencing company, and a treatment method selection (that is, determination of administration drug) is also performed on the basis of a report of the oncogene panel test and is selected from existing drugs. Therefore, there is no need to associate patient identification information (for example, patient ID) or genome data with pharmaceutical identification information (for example, pharmaceutical ID).

In Car-T, it is not necessary to analyze patient gene data, and in principle, it is sufficient to manage the process only between two parties of a factory and a hospital, and since there is no genetic analysis institution (for example, sequence vendor) or recipe creation institution, cooperation thereof is not considered. In a case of personalized cancer vaccine therapy, since vaccines span a plurality of organizations and/or systems, their management is necessary, and process management and information sharing are important. However, in the Car-T supply chain, only physical specimen transportation and sharing of some data accompanying the physical specimen are performed, and process management and information sharing are insufficient.

(1) As described above, conventionally, there is no need to manage the patient, the genome of the patient, and the vaccine to be administered to the patient in association with each other, and thus there is a further problem that a method for appropriately managing the patient, the genome of the patient, and the vaccine to be administered to the patient is desired. In order to solve this problem, the present embodiment provides a management method for the patient, the genome of the patient, and the vaccine to be administered to the patient.

(2) In addition, there is a further problem that, unlike existing medicine, there is a need to manage information of each step (for example, quality information, success/failure of each step, and the like) in order to span a plurality of organizations and/or systems. To solve this problem, the management system of the present embodiment provides a pipeline management function for managing information of each step (for example, quality information, success/failure of each step, and the like).

(3) Since there is a possibility that the supply chain extends across multiple countries, there is a further problem that appropriate management of personal information is required in each country. To solve this problem, in the present embodiment, access restriction is provided for each institution (system).

The recipe is, for example, peptide sequence data of neoantigens, data of proteins, or aggregate data of administered compounds. Hereinafter, in the present embodiment, a description is given in which it is assumed that the administration item is a vaccine as an example and the recipe is peptide sequence data of neoantigens.

FIG. 1 is a schematic block diagram of an information processing system according to a first embodiment. As illustrated in FIG. 1, the information processing system S includes hospital systems 1-1, . . . , 1-N (N is a natural number), a genetic analysis institution system 2, a recipe creation institution system 3, a vaccine manufacturing institution system 4, and a management system 5 connected to these systems via a communication circuit network CN. Each system includes a storage device, and a database is built in the storage device as an example. The hospital system 1-1, . . . , 1-N is also collectively referred to as a hospital system 1.

Here, the hospital system 1 is a computer system managed by a hospital, and includes one or more computers. The genetic analysis institution system 2 is a computer system managed by a genetic analysis institution (also simply referred to as an analysis institution), and includes one or more computers. The genetic analysis institution is, for example, a sequence vendor. The recipe creation institution system 3 is a computer system managed by a recipe creation institution (also simply referred to as a creation institution), and includes one or more computers. The recipe creation institution is, for example, a personalized cancer vaccine (PCV) prediction vendor. The vaccine manufacturing institution system 4 is a computer system managed by a vaccine manufacturing institution (also simply referred to as a manufacturing institution), and includes one or more computers. The vaccine manufacturing institution is, for example, a vaccine manufacturing vendor.

A hospital terminal 11-*i* is connected to the hospital system 1-*i* (i is an integer from 1 to N) for communication. The hospital terminal 11-*i* is a terminal provided in a hospital and operated by a medical personnel such as a doctor, a nurse, and others. Hereinafter, the hospital terminals 11-1, . . . , . . . and 11-N are also collectively referred to as the hospital terminal 11. An analyst terminal 21 is connected to the genetic analysis institution system 2 for communication. A creator terminal 31 is connected to the recipe creation institution system 3 for communication. A manufacturer terminal 41 is connected to the vaccine manufacturing institution system 4 for communication.

Hereinafter, the hospital terminal 11, the analyst terminal 21, the creator terminal 31, and the manufacturer terminal 41 may be collectively referred to as the terminal. Note that, here, a case where each of the genetic analysis institution system 2, the recipe creation institution system 3, and the vaccine manufacturing institution system 4 is one will be described as an example, and a plurality of genetic analysis institution systems 2, recipe creation institution systems 3, and vaccine manufacturing institution systems 4 may be provided similarly to the hospital system 1.

The management system 5 is a system managed by an administrator, and notifies the terminal (for example, the hospital terminal 11, the analyst terminal 21, the creator terminal 31, and the manufacturer terminal 41) of completion or progress in each step.

Figure 2:
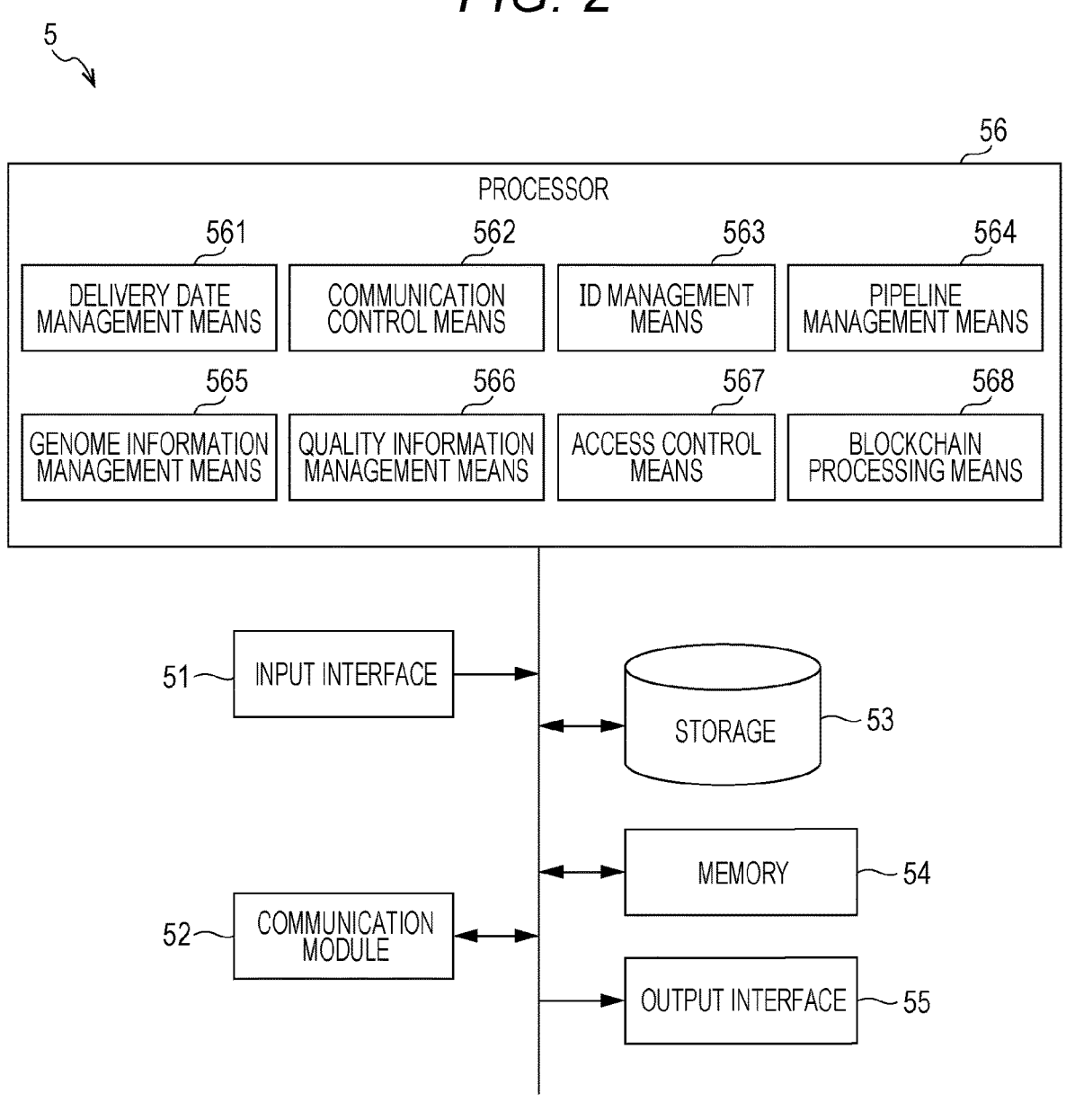
FIG. 2 is a schematic block diagram of a management system according to the present embodiment.

FIG. 2 is a schematic block diagram of a management system according to the present embodiment. As illustrated in FIG. 2, the management system 5 includes, for example, an input interface 51, a communication module 52, a storage 53, a memory 54, an output interface 55, and a processor 56.

The input interface 51 receives an input from the administrator of the management system 5 and outputs an input signal corresponding to the received input to the processor 56.

The communication module 52 is connected to the communication circuit network CN and communicates with the hospital terminal 11, the analyst terminal 21, the creator terminal 31, and the manufacturer terminal 41. This communication may be wired or wireless, and a communication being wired is described.

The storage 53 is an example of a storage device, and stores programs and various data to be read and executed by the processor 56. In the present embodiment, as an example, a database is constructed in the storage 53.

The memory 54 temporarily holds data and programs. The memory 54 is a volatile memory, and is, for example, a random access memory (RAM).

The output interface 55 can be connected to an external device and can output a signal to the external device.

The processor 56 loads a program into a memory (not illustrated) and executes a series of instructions included in the program, thereby functioning as a delivery date management means 561, a communication control means 562, an ID management means 563, a pipeline management means 564, a genome information management means 565, a quality information management means 566, an access control means 567, and a blockchain processing means 568.

In the delivery date management means 561, the management system determines a predicted delivery date or a predicted required time when the administration item is delivered to a hospital, using an estimated time or an actual required time when the analysis institution analyzes the gene of the specimen of the patient, an estimated time or an actual required time when the creation institution creates a recipe of the administration item (for example, vaccine) to the patient from the genetic analysis result, and/or an estimated time or an actual required time when the manufacturing institution manufactures the administration item according to the recipe.

The communication control means 562 transmits information for displaying the predicted delivery date or the predicted required time to the terminal (for example, the hospital terminal 11, the analyst terminal 21, the creator terminal 31, or the manufacturer terminal 41). As a result, the information for displaying the predicted delivery date or the predicted required time of the administration item (for example, vaccine) for personalized medicine is displayed on the terminal, so that the delivery date of the administration item for personalized medicine can be grasped.

The ID management means 563 manages a hospital ID which is an example of hospital identification information for identifying a hospital, a patient ID which is an example of patient identification information for identifying a patient, a specimen ID which is an example of specimen identification information for identifying a specimen, a common ID for common management, a recipe ID which is an example of recipe identification information for identifying a recipe, and a vaccine ID which is an example of vaccine identification information for identifying a vaccine. For example, the ID management means 563 accumulates the patient, the genome information, and the vaccine information in association with the common ID, so that cooperation among a plurality of systems can be integrally performed.

The pipeline management means 564 manages progress information of each step (for example, success/failure in each step) of genetic analysis, recipe creation, and vaccine manufacture. For example, the pipeline management means 564 acquires success/failure in each step of vaccine manufacture in real time, and notifies the terminal of the success/failure in each step in response to a request from the terminal. As a result, the administrator, the doctor, and the person in charge of each institution can share the success/failure in each step of vaccine manufacture in real time.

In addition, for example, the pipeline management means 564 automatically acquires the occurrence of an error from the hospital system 1, the genetic analysis institution system 2, the recipe creation institution system 3, and the vaccine manufacturing institution system 4. This makes it possible to quickly detect an abnormality in the process. When an error occurs, the pipeline management means 564 notifies the system of the subsequent step and the hospital system of the error. Further, the pipeline management means 564 notifies the system of the subsequent step to stop the subsequent process, so that the recovery time at the time of abnormality can be expected to be shortened.

The genome information management means 565 manages genome information of the patient.

The quality information management means 566 manages data related to the quality of vaccine manufacture. For example, the quality information management means 566 notifies the hospital terminal 11 of the data in response to a request from the hospital terminal 11. This allows the doctor to refer to this data, and the doctor can use the data to make vaccine administration decisions.

For example, in a case where the quality information management means 566 receives quality information on a specimen, quality information on a gene sequence, quality information on a recipe, and/or quality information on a vaccine from a hospital system, an analysis institution system, a creation institution system, and/or a manufacturing institution system, the quality information management means 566 stores the received information in the storage 53.

The genome information management means 565 and the quality information management means 566 can detect falsification by leaving a history of browsing and deleting the database.

The access control means 567 restricts information that can be accessed for each institution. In addition, the access control means 567 may determine an access source country, and restrict the browsing of the patient information by determining an access authority (institution, position, name, etc.) using a certificate.

The blockchain processing means 568 writes and manages an update history and/or update data of the storage 53 in a blockchain. The update history includes, for example, a history of browsing and deleting the database of the storage 53. This makes it difficult to falsify data during the step.

In addition, the update data includes, for example, data related to steps of the embodiment (for example, various IDs, vaccine manufacture progress information, patient genome information, data related to vaccine manufacture quality, and the like). As a result, even in a case the data in the storage 53 is damaged, the data can be restored from the blockchain.

Note that the blockchain processing means 568 may store only the update history in the blockchain. As a result, since the update data is not stored in the blockchain, the confidentiality of the update data can be ensured.

In the present embodiment, in a case where the management system 5 receives the specimen ID from the hospital system 1, the management system 5 assigns the common ID, only the management system 5 manages data with the common ID, the hospital system 1 and the genetic analysis institution system 2 manage data with the specimen ID, the recipe creation institution system 3 manages data with the recipe ID, and the vaccine manufacturing institution system 4 manages data with the vaccine ID.

FIG. 3 is a diagram illustrating a schematic configuration of a database of each system in the present embodiment. As illustrated in FIG. 3, a table T5 of the management system stores records of a set of a hospital ID for identifying a hospital, a patient ID for identifying a patient, a specimen ID for identifying a specimen, a common ID for managing data, a sequence file name which is a name of a sequence file storing a gene sequence sequenced from the specimen of the patient, a recipe ID for identifying a vaccine recipe, a recipe file name which is a name of a recipe file storing the vaccine recipe, and a vaccine ID for identifying a vaccine. Here, the sequence file is stored, for example, in a predetermined directory for the sequence file. In addition, the recipe file is stored, for example, in a predetermined directory for the recipe file.

Here, the specimen ID may be given to a normal tissue or blood of a patient, or may be given to a cancer tissue of a patient. Here, as an example, the specimen ID given to the normal tissue or blood of the patient and the specimen ID given to the cancer tissue of the patient are different only at the last end.

The sequence file includes a file storing a sequence of DNA of a normal tissue (also referred to as normal DNA), a file storing a sequence of DNA of a cancer tissue (also referred to as cancer DNA), and a file storing a sequence of RNA of a cancer tissue (also referred to as cancer RNA). Each sequence file name is stored in the table T5, and each sequence file is stored in the storage 53.

The table T1 of the hospital system stores a record of a set of the patient ID, the specimen ID, and the vaccine ID. Here, for example, when notified from the management system 5, the vaccine ID is stored in the table T1.

The table T2 of the genetic analysis institution system 2 stores a record of a set of the specimen ID and the sequence file name which is a name of the sequence file. Here, the sequence file is stored, for example, in a predetermined directory for the sequence file. As a result, the genetic analysis institution system 2 can refer to the sequence file name of the table T2 and read the sequence file.

The table T3 of the recipe creation institution system 3 stores a record of a set of the sequence file name which is a name of the sequence file, the recipe ID, and the recipe file name which is a name of the recipe file. Here, the sequence file is stored, for example, in a predetermined directory for the sequence file. As a result, the recipe creation institution system 3 can refer to the sequence file name and read the sequence file. In addition, the recipe file is stored, for example, in a predetermined directory for the recipe file. As a result, the recipe creation institution system 3 can refer to the recipe file name and read the recipe file.

The table T4 of the vaccine manufacturing institution system 4 stores a record of a set of the recipe file name which is a name of the recipe file, and the vaccine ID. Here, the recipe file is stored, for example, in a predetermined directory for the recipe file. As a result, the vaccine manufacturing institution system 4 can refer to the recipe file name and read the recipe file.

Figure 4:
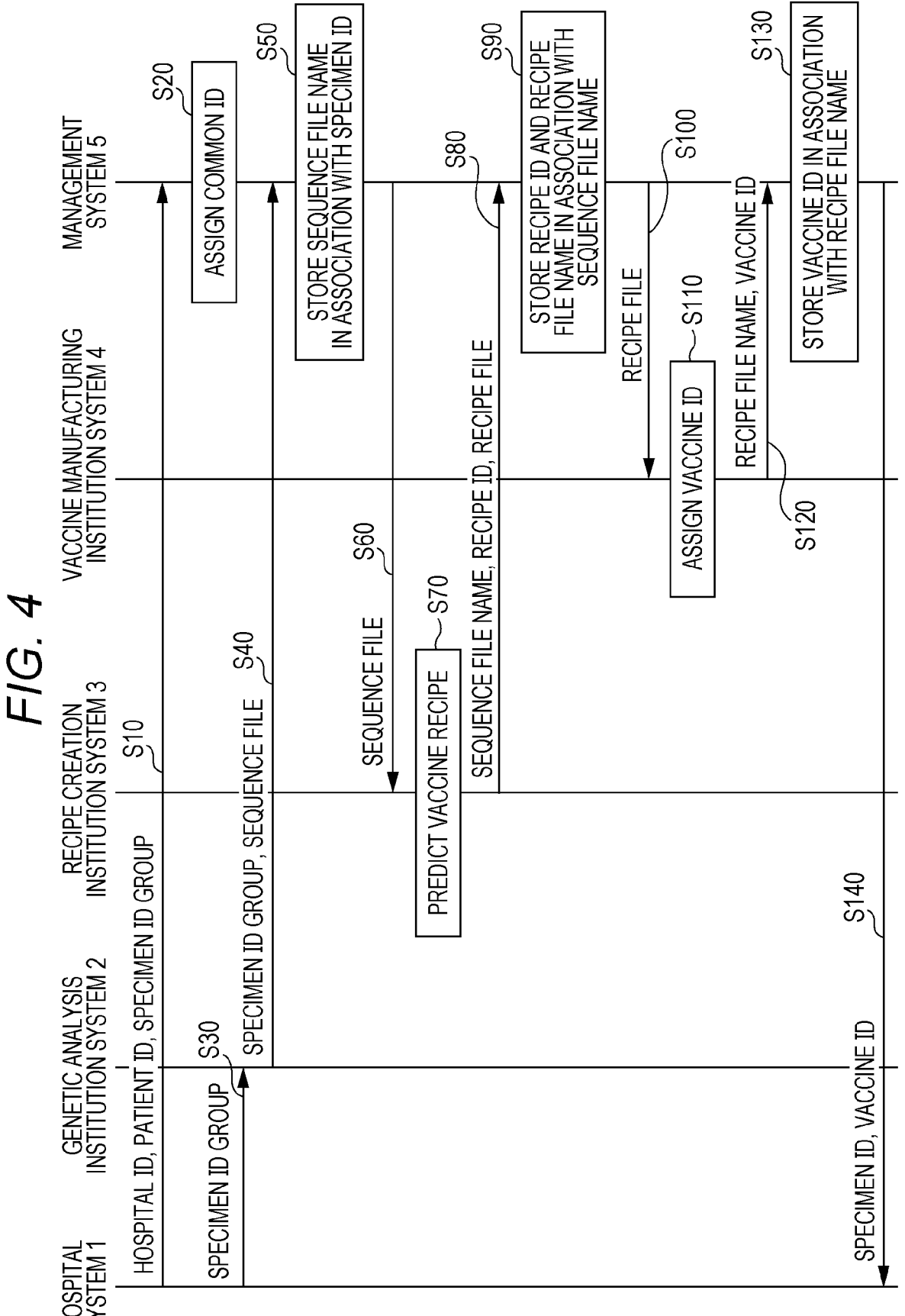
FIG. 4 is an example of a sequence diagram according to the present embodiment.

FIG. 4 is an example of a sequence diagram according to the present embodiment. Hereinafter, the process of the processor of each system will be described, and the processor is not explicitly described from the viewpoint of readability.

(Step S10) First, the hospital system 1 assigns a patient ID for identifying a target patient and a specimen ID group for identifying a specimen group (for example, normal tissue or blood and cancer tissue) of the target patient, and stores them as a new record in a table T1 (see FIG. 3) of the hospital system 1. Here, as an example, it is assumed that the high-order four digits of the specimen ID are not the same as other specimen IDs. Furthermore, the hospital system 1 transmits, for example, a set of the hospital ID for identifying the hospital (or the hospital system 1), the patient ID and the specimen ID to the management system 5.

(Step S20) In a case where the management system 5 receives the set of the hospital ID, the patient ID, and the specimen ID, the management system 5 assigns a common ID that is not the same as other common IDs, associates the common ID with the received set of the hospital ID, the patient ID, and the specimen ID, and stores the common ID as a new record in the table T5 (see FIG. 3) of the management system 5.

(Step S30) Next, the hospital system 1 transmits the specimen ID group transmitted in step S10 to the genetic analysis institution system 2. At the same time, the hospital side sends the target specimen group (for example, normal tissue or blood and cancer tissue) to the genetic analysis institution.

The specimen ID group is not limited to be transmitted by communication, and the specimen ID may be stored in a nonvolatile memory (for example, a flash memory) and sent together with the specimen.

(Step S40) In a case of accepting the specimen ID group and the specimen, the genetic analysis institution executes a gene sequence on the specimen, generates a sequence file storing the gene sequence, and stores the sequence file in a predetermined directory for the sequence file. Here, as an example, a naming rule is defined in such a manner that the sequence file name is not the same as other sequence file names. For example, the sequence file name includes the high-order four digits of the specimen ID. As a result, since the high-order four digits of the specimen ID are not the same as other specimen IDs, it is possible to avoid overlapping of sequence file names. The genetic analysis institution system 2 stores a new record of the set of the specimen ID and the sequence file name in the table T2. The genetic analysis institution system 2 transmits the sequence file and the specimen ID group to the management system 5.

(Step S50) In a case where the management system 5 receives the sequence file and the specimen ID, the management system 5 searches a record from the table T5 of the management system 5 using the received specimen ID as a key, and updates the sequence file name of the record with the name of the received sequence file. In addition, the management system 5 stores the sequence file in a predetermined directory for the sequence file. As a result, since the specimen ID is associated with the common ID in advance, the sequence file is also associated with the common ID.

(Step S60) The management system 5 transmits the sequence file to the recipe creation institution system 3, for example. The recipe creation institution system 3 receives the sequence file.

(Step S70) In a case where the recipe creation institution system 3 receives the sequence file, the recipe creation institution system 3 predicts the vaccine recipe using the gene sequence stored in the sequence file. Specifically, for example, the recipe creation institution system 3 predicts a peptide sequence. The recipe creation institution system 3 stores the vaccine recipe obtained from the prediction in a recipe file. Here, as an example, a naming rule is defined in such a manner that the recipe file name is not the same as other recipe file names.

(Step S80) The recipe creation institution system 3 assigns a recipe ID that is not the same as other recipe IDs, and stores a set of the file name of the sequence file received in step S60, the recipe ID, and the recipe file generated in step S70 as a new record in the table T3 of the recipe creation institution system. Then, the recipe creation institution system 3 transmits the set of the file name of the sequence file, the recipe ID, and the recipe file to the management system 5.

(Step S90) In a case where the management system 5 receives the information transmitted in step S80, the management system 5 extracts a record using the sequence file name as a key in the table T5, and updates the recipe ID and the recipe file name of the record with the received recipe ID and the received file name of the recipe file. In this manner, the management system 5 stores the recipe ID and the recipe file name in association with the sequence file name. In addition, the management system 5 stores the recipe file in a directory determined in advance for the recipe file.

(Step S100) The management system 5 transmits the received recipe file to the vaccine manufacturing institution system 4.

(Step S110) In a case where the vaccine manufacturing institution system 4 receives the recipe file, the vaccine manufacturing institution manufactures a vaccine based on the recipe stored in the recipe file. Then, the vaccine manufacturing institution system 4 assigns a vaccine ID to the manufactured vaccine.

(Step S120) The vaccine manufacturing institution system 4 transmits a set of the recipe file name of the received recipe file and the vaccine ID assigned in step S110 to the management system 5. Note that the recipe file itself may be transmitted instead of the recipe file name.

In addition, the vaccine manufacturing institution system 4 adds a record of a set of the recipe file name and the vaccine ID to the table T4 (see FIG. 3) of the vaccine manufacturing institution system.

(Step S130) The management system 5 receives the set of the recipe file name and the vaccine ID. Then, the management system 5 searches the record of the table T5 of the management system using the received recipe file name as a key, and updates the vaccine ID of the record obtained from the search with the received vaccine ID. In this way, the management system 5 stores the received vaccine ID in association with the received recipe file name.

(Step S140) The management system 5 reads the specimen ID and the hospital ID stored in the same record as the received vaccine ID in the table T5 of the management system, and transmits the vaccine ID and the read specimen ID (or specimen ID group) to the hospital system 1 identified by the hospital ID. The hospital system 1 receives the set of the vaccine ID and the specimen ID, searches the table T1 of the hospital system using the specimen ID as a key (see FIG. 3), and updates the vaccine ID of the record obtained from the search with the received vaccine ID.

Vaccine Order Placement Screen

Figure 5:
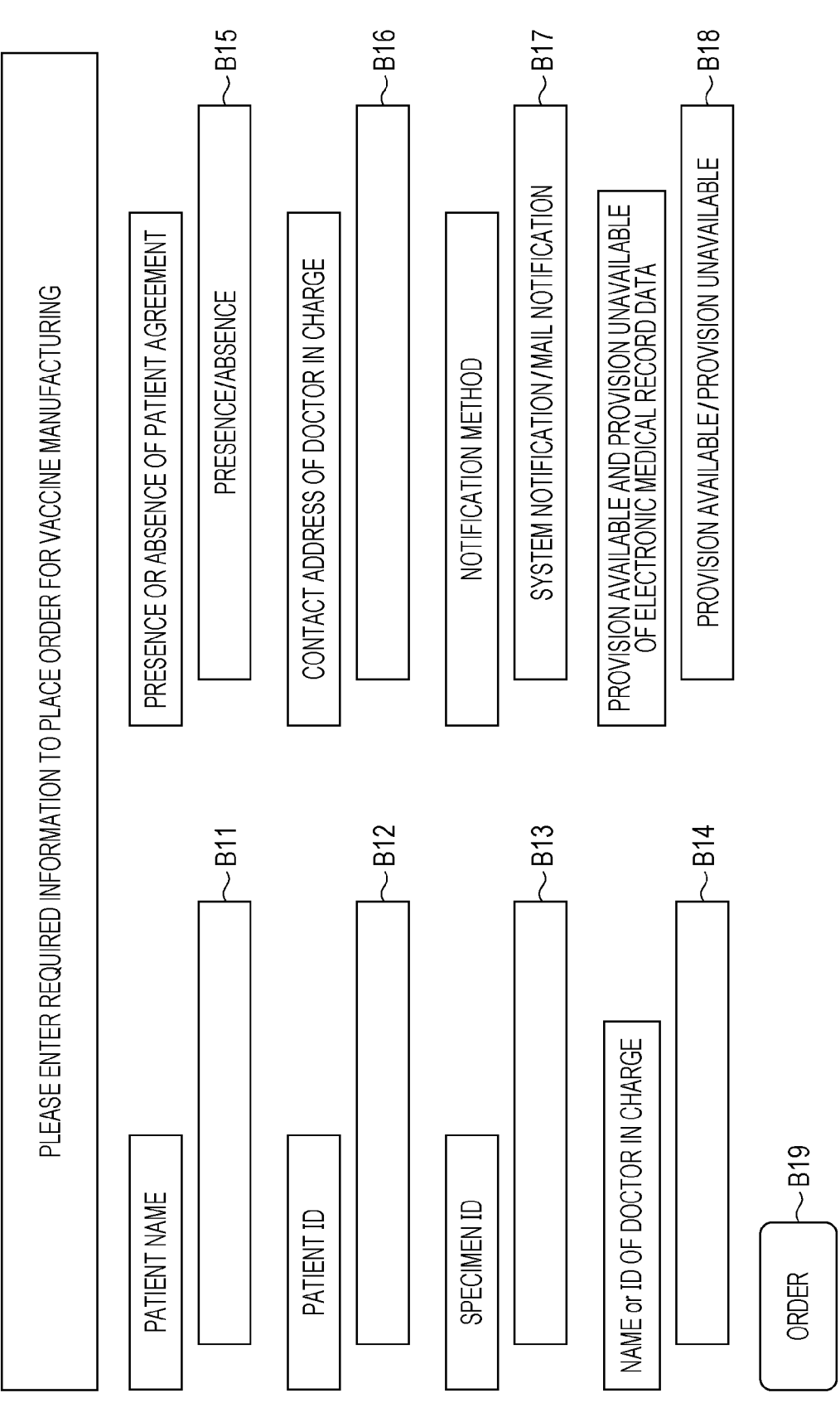
FIG. 5 is an example of a vaccine order placement screen displayed on a hospital terminal.

Next, a vaccine order placement screen displayed on the hospital terminal 11 will be described with reference to FIG. 5. FIG. 5 is an example of a vaccine order placement screen displayed on a hospital terminal 11. As illustrated in FIG. 5, the vaccine order placement screen G1 displays a text box B11 for inputting a patient name, a text box B12 for inputting a patient ID, a text box for inputting a specimen ID, a text box for inputting the name or ID of the doctor in charge, a select box B15 for the presence or absence of patient agreement, a text box B16 for inputting a contact address (for example, an e-mail address) of the doctor in charge, a text box B17 for selecting a notification method from the management system 5, a text box B18 for inputting provision available and provision unavailable of electronic medical record data, and an order button B19.

In a case where a system notification is selected as a notification method, information (for example, progress information, an error, and the like) from the management system 5 is notified to the hospital system 1. On the other hand, in a case where an e-mail notification is selected as the notification method, information (for example, progress information, an error, and the like) from the management system 5 is notified by an e-mail addressed to the e-mail address of the doctor in charge. In a case where "provision available" is selected for the provision of the electronic medical record data, the electronic medical record data of the patient is provided to the management system 5. On the other hand, in a case where "provision unavailable" is selected for the provision of the electronic medical record data, the electronic medical record data of the patient is not provided to the management system 5.

In a case where the order button B19 is pressed, the hospital system 1 transmits the input information to the management system 5 in step S10 of FIG. 4. At that time, in a case where "provision available" is selected for the provision of the electronic medical record data, the electronic medical record data of the patient may be transmitted to the management system 5.

The specimen ID may be automatically determined and automatically input by the hospital system 1.

Progress Management Screen in Hospital Terminal

Subsequently, the progress management screen displayed on the hospital terminal 11 will be described with reference to FIG. 6. As an example, the management system 5 manages the patient ID, the status, and the progress in a database in association with each other. In response to the request from the hospital terminal 11, information for displaying the progress management screen is replied from the management system 5, and the progress management screen is displayed on the hospital terminal 11 on the basis of the information.

FIG. 6 is an example of a progress management screen displayed on the hospital terminal. As illustrated in FIG. 6, the progress management screen G2 displays the patient ID, the status of the target vaccine, the progress of the step of the target vaccine, the delivery date/delivery date certainty factor, and the administration schedule of the target vaccine. The status includes, for example, "In Production" indicating that vaccine preparation is in progress, "Error" indicating that an error during a step, and "Completed" indicating that the vaccine has been administered. Here, "In Production" is displayed in bold as an example of visually highlighted display. As a result, the medical person who uses the hospital terminal can grasp that the vaccine is being prepared. Here, the visually highlighted display is, for example, decoration of a character itself such as a character color being different from others or a character thickness being different from others, decoration of a background of a character such as a background color or a background pattern of a character being different, decoration around a character such as an underline or a bystander, or a combination thereof. Note that the status is not limited to the visually highlighted display, and for example, one of "In Production" indicating that the vaccine preparation is in progress, "Error" indicating an error during a step, and "Completed" indicating that the vaccine has been administered may be displayed as the status.

The progress of the target vaccine steps is indicated as to which step is being performed at the present time. The progress includes, for example, specimen transport in progress, sequence in progress, sequence completed, PCV prediction in progress, PCV prediction completed, vaccine manufacture in progress, vaccine manufacture completed, vaccine transport in progress, arrived at hospital, patient administrated, and manufacture interrupted, and here, "PCV prediction" is displayed in bold as an example of visually highlighted display. As a result, the medical person who uses the hospital terminal can grasp that the vaccine recipe is being predicted. Here, as described above, the visually highlighted display is, for example, decoration of a character itself such as a character color being different from others or a character thickness being different from others, decoration of a background of a character such as a background color or a background pattern of a character being different, decoration around a character such as an underline or an emphasis dot, or a combination thereof. Note that the progress is not limited to the visually highlighted display, and for example, one of the above may be displayed as the progress.

On the progress management screen G2, a text box B21 and a send button B22 for the doctor to update the progress are displayed. When the send button B22 is pressed, the information input in the text box B21 is transmitted to the management system 5, and the database of the management system 5 is updated.

As an example, an image indicating the progress status is displayed at the center on the progress management screen G2. Here, the PCV prediction vendor is indicated to be in progress in the creation of the vaccine recipe. In addition, the progress management screen G2 displays the remaining period until vaccine provision. The remaining period until the vaccine provision is determined by the management system 5. Hereinafter, a specific example of a method for determining the predicted delivery date or the predicted required time of the vaccine (including the remaining period until the vaccine provision described above) will be described.

Determination Method 1 of Predicted Delivery
Date or Predicted Required Time: Case of Using
Predetermined Value First, in a genetic analysis institution (for example, a sequence vendor), a recipe creation institution (for example, a vaccine recipe prediction system vendor), and a vaccine manufacturing institution (for example, a vaccine manufacturing system vendor), the time taken for each system to accept data and specimens from the previous step and deliver a product to the subsequent step is collected (how long it takes from the vendor is interrogated in advance). Further, the time generated in transferring from one step to another step is collected (for example, from transporters), and the management system 5 determines the predicted delivery date. At this time, the estimated required times for all steps and for each step are calculated and stored in the storage 53 of the management system 5. The management system 5 may determine the remaining period until the vaccine provision by summing the estimated required time generated in the remaining steps until the vaccine provision and the estimated required time generated in transferring from one remaining step to another remaining step.

The management system 5 detects a delay and notifies the hospital system 1 or the doctor in charge in a case where the time actually taken by a certain step exceeds the stored estimated required time of each step. The notification method to the doctor in charge is, for example, notification to an e-mail address of the doctor in charge, notification to an external application by API cooperation, notification on a system screen, or the like.

Determination Method 2 of Predicted Delivery
Date or Predicted Required Time: Case of Using
Predetermined Value First, from a genetic analysis institution (for example, sequence vendor), a recipe creation institution (for example, vaccine recipe prediction system vendor), and a vaccine manufacturing institution (for example, vaccine manufacturing system vendor), the time taken for each system to accept data and/or specimens from the previous step and transfer a product to the subsequent step is collected. In this case, it is preferable that the system automatically collects the time taken in each step, and the management system 5 preferably acquires these collected times from each system.

Further, the management system 5 calculates a time generated in transferring from one step to another step For example, the management system 5 may calculate a time by subtracting the time taken by each of two consecutive steps from the actual total required time of the two steps. The management system 5 may calculate an average value or a median value of the collected actual required times of each step as an estimated required time and store the calculated average value or median value in the storage 53 of the management system 5. In addition, the management system 5 may determine the average value or the median value of the entire required time as an estimated delivery date by using each of the entire actual required times, and store the predicted delivery date in the storage 53 of the management system 5.

In addition, the management system 5 may determine the remaining period until the vaccine provision by adding the average value or the median value of the actual required times of the remaining steps until the vaccine provision and the average value or median of the actual required times generated in transferring from one remaining step to another remaining step.

In addition, when the actual required time has been sufficiently collected, the management system 5 may determine the estimated delivery date by inputting at least one of a gene fragment amount and/or the base amount of genes to be read, the sequence data amount, and a genetic mutation amount to the trained machine learning model. Here, the machine learning model is trained by using learning data in which at least one of a gene fragment amount and/or the base amount of gene to be read, the sequence data amount, and a genetic mutation amount is input and an estimated delivery date is output.

The management system 5 may detect a delay and notify the hospital system 1 or the doctor in charge in a case where the time actually taken by a certain step exceeds the stored estimated required time of each step. The notification method to the doctor in charge is, for example, notification to an e-mail address of the doctor in charge, notification to an external application by API cooperation, notification on a system screen, or the like.

Modification of Determination Method of Predicted Delivery Date or Predicted Required Time The delivery date management means 561 determines an estimated time for analyzing the gene according to the number of gene fragments (reads) and/or the base amount of gene to be read obtained from the specimen.

Alternatively, the delivery date management means 561 may determine the estimated time for creating the recipe according to the sequence data amount (for example, the capacity of the sequence file) obtained as a result of the genetic analysis.

Alternatively, the delivery date management means 561 may determine an estimated time for creating the recipe according to a genetic mutation amount.

Alternatively, the delivery date management means 561 may determine the estimated time for creating the recipe according to the name of the organ from which the specimen was obtained.

Since there is some ambiguity regarding the determination of the delivery date, the management system 5 may notify the certainty factor of the delivery date. There are, for example, the following two methods for calculating the certainty factor.

First Example of Calculation Method for Delivery Date Certainty Factor: Method of Increasing Certainty Factor for Each Completed Step The management system 5 increases the certainty factor of the delivery date when the steps such as the sequence step, the vaccine recipe prediction step, and the vaccine manufacturing step or other steps are transitioned (for example, from 20% to 40% when the sequence step is completed, etc.).

Second Example of Calculation Method for Delivery Date Certainty Factor: Increasing Certainty Factor from Actual Values The management system 5 collects the actual required time of each step, determines an average value or a median value thereof as a threshold value for each step, and decreases the certainty factor in a case where the determined threshold is below the threshold value corresponding to each step, and increases the certainty factor in a case where the determined threshold is above the threshold value corresponding to each step. In addition, the management system 5 may learn the actual required time of each step by machine learning or the like and use the prediction result as the certainty factor.

Patient Administration Schedule

The management system 5 may set the patient administration date from the terminal 1 in a case where the certainty factor exceeds a set value (for example, 80%). For example, in a case where the certainty factor exceeds a set value (for example, 80%), the management system 5 may change the progress management screen G2 in such a manner that the hospital side can determine the scheduled administration date for the target patient from the calendar, or may change the progress management screen G2 in such a manner that a plurality of candidates can be designated.

Example of Progress Management Screen of Analyst Terminal, Creator Terminal or Manufacturer Terminal FIG. 7 is an example of a progress management screen displayed on the analyst terminal, the creator terminal, or the manufacturer terminal. As illustrated in FIG. 7, the progress management screen G3 displays the patient ID, the status of the target vaccine, and the progress of the step of the target vaccine. Here, the status includes, for example, "In Production" indicating that vaccine preparation is in progress, "Error" indicating that an error during a step, and "Completed" indicating that the vaccine has been administered. Here, as an example, "In Production" which is an example of the current status is displayed in bold as an example of visually highlighted display. As a result, the medical person who uses the hospital terminal can grasp that the vaccine is being prepared. Here, as described above, the visually highlighted display is, for example, decoration of a character itself such as a character color being different from others or a character thickness being different from others, decoration of a background of a character such as a background color or a background pattern of a character being different, decoration around a character such as an underline or an emphasis dot, or a combination thereof. Note that the status is not limited to the visually highlighted display, and for example, one of "In Production" indicating that the vaccine preparation is in progress, "Error" indicating an error during a step, and "Completed" indicating that the vaccine has been administered may be displayed as the status.

The progress of the target vaccine steps is indicated as to which step is being performed at the present time. The progress includes, for example, specimen transport in progress, sequence in progress, sequence completed, PCV prediction in progress, PCV prediction completed, vaccine manufacture in progress, vaccine manufacture completed, vaccine transport in progress, arrived at hospital, patient administrated, and manufacture interrupted, and here, "PCV prediction" is displayed in bold as an example of visually highlighted display. As a result, the medical person who uses the hospital terminal can grasp that the vaccine recipe is being predicted. Here, as described above, the visually highlighted display is, for example, decoration of a character itself such as a character color being different from others or a character thickness being different from others, decoration of a background of a character such as a background color or a background pattern of a character being different, decoration around a character such as an underline or an emphasis dot, or a combination thereof. Note that the progress is not limited to the visually highlighted display, and for example, one of the above may be displayed as the progress.

In addition, on the progress management screen G3, a text box B31 and a send button B32 for each user to update the progress are displayed. When the send button B32 is pressed, the information input in the text box B31 is transmitted to the management system 5, and the database of the management system 5 is updated.

As an example, an image indicating the progress status is displayed at the center on the progress management screen G3. Here, the PCV prediction vendor is indicated to be in progress in the creation of the vaccine recipe. In addition, the progress management screen G3 displays the remaining period until vaccine provision. As described above, the remaining period until the vaccine provision is determined by the management system 5.

Access Control Target Data

Next, the access control target data will be described. The access control target data includes, for example, the following data:

(1) Common ID (2) Sequence data (Information of DNA and RNA extracted from a patient specimen. For PCV prediction, three types of cancer DNA, normal DNA, and cancer RNA are included.)

(3) Clinical data (Data registered in the electronic medical record of the hospital system. Collect data in the range agreed by hospitals and patients. For example, medical history, numerical values of preliminary examination, medical interview sheet, and the like.)

(4) Sequence report (Data issued by a genetic analysis institution and related to the quality of the genome sequence. For example, the average read length, RIN value, and the like of DNA.)

(5) Quality Control (QC) data and analysis intermediate data (Intermediate data when a recipe creation institution system or a genetic analysis institution system processes genome data or data related to prediction or quality of genome analysis, data obtained by performing QC of genome data and its intermediate data as preprocessing, and/or data obtained by performing QC of a PCV recipe itself. For example, the average read length of DNA, the presence or absence of contamination, the reliability of HLA typing, the number of candidates included in a PCV recipe, and the like.)

(6) Vaccine manufacturing quality data (Data related to the quality when a vaccine manufacturing institution manufactures a vaccine based on a vaccine recipe that is digital data. For example, the temperature at the time of manufacturing the vaccine, the purity of the peptide, the acceptance/rejection of the shipping determination, and the like.)

(7) Laboratory data (Refer to laboratory experimental data for performing validation of vaccine recipes, laboratory experimental data for performing validation for adding candidate epitopes to vaccine recipes. For example, measured binding value of epitope, immunogenicity value, etc.)

(8) Monitoring data after administration (Data indicating the health status of the patient after administration of the vaccine. For example, recurrence biomarkers, test items for cancer screening, and the like.)

(9) System log (The raw log can be viewed, for example, only by an administrator who operates the present system, and becomes original information of notification at the time of an error or at the time of updating the progress of the vaccine manufacturing process.)

Incorporation in Laboratory

An actual experiment in the laboratory may be incorporated in the process in addition to or instead of the recipe creation institution. Laboratory data can also be used to (1) validate the accuracy of the recipe creation institution system or (2) as a supplement for a vaccine recipe base on the actual experiment.

List of Access Restriction

Next, an example of whether or not each organization can access the nine types of data to be accessed will be described with reference to FIG. 8. FIG. 8 is an example of a list of access restrictions on data to be accessed. In the list of FIG. 8, the accessibility and inaccessibility of each of the hospital, the genetic analysis institution, the recipe creation institution, the vaccine manufacturing institution, the administrator of the management system 5, and the laboratory vendor is illustrated for the nine types of data to be accessed. In the list of FIG. 8, o represents accessibility, and x represents inaccessibility. The storage 53 of the management system 5 may store the access restrictions in the table of FIG. 8 as a table, and the access restrictions may be based on the stored table.

Search Result Screen in Hospital Terminal

Next, an example of a search result screen in the hospital terminal 11 will be described with reference to FIG. 9. FIG. 9 is an example of a search result screen displayed on the hospital terminal. On the search result screen G4 in FIG. 9, a text box B41 for inputting a patient ID and a search button B42 are illustrated. The search result screen G4 in FIG. 9 is an example of a result screen obtained by inputting the patient ID into the text box B41 and pressing the search button B42.

For the patient ID of the search target, the stator, the progress, the sequence report reference URL, the QC data reference URL, the vaccine manufacturing quality data reference URL, the laboratory data reference URL, the clinical data (before administration) reference URL, and the monitoring data reference URL of the vaccine are displayed. It is displayed that some data cannot be browsed due to lack of authority and cannot be disclosed as an example.

A management system 5 according to the present embodiment includes: a delivery date management means that determines a predicted delivery date or a predicted required time when an administration item is delivered to a hospital by using an estimated time or an actual required time when an analysis institution analyzes a gene of a specimen of a patient, an estimated time or an actual required time when a creation institution creates a recipe of the administration item to a patient from a genetic analysis result, and an estimated time or an actual required time when a manufacturing institution manufactures the administration item according to the recipe; and a communication control means that transmits information for displaying the predicted delivery date or the predicted required time to a terminal.

In other words, the management method according to the present embodiment includes: a determination step in which the management system determines a predicted delivery date or a predicted required time when an administration item is delivered to a hospital by using an estimated time or an actual required time when an analysis institution analyzes a gene of a specimen of a patient, an estimated time or an actual required time when a creation institution creates a recipe of the administration item to a patient from a genetic analysis result, and/or an estimated time or an actual required time when a manufacturing institution manufactures the administration item according to the recipe; and a transmission step in which information for displaying the predicted delivery date or the predicted required time is transmitted to a terminal.

The management method according to the present embodiment further includes a step of, in a case where a request for a progress status of an administration item (for example, a vaccine) is received from a terminal (for example, the hospital terminal 11, the analyst terminal 21, the creator terminal 31, or the manufacturer terminal 41), replying in which the management system replies information for displaying the progress status to the terminal. As a result, the terminal displays the progress status by using the replied information.

The management method according to the present embodiment further includes, in the step of replying, a step of replying a progress status within a range permitted by a browsing authority assigned to an institution to which a terminal that has requested the progress status belongs, a browsing authority being assigned to each institution and stored in a storage device.

The management method according to the present embodiment further includes a step of, in a case where the predicted delivery date or the predicted required time is delayed, notifying a doctor terminal logged in to a service provided by the management system by a doctor in charge of the patient or a doctor in charge of the patient.

The management method according to the present embodiment further includes a step of allowing a reception of setting an administration schedule to the patient when a certainty factor of a delivery date exceeds a reference.

The management method according to the present embodiment further includes a step in which the management system 5 transmits a gene sequence data to the recipe creation institution system 3 in a case where the gene sequence data is received from the analysis institution; and a step in which the management system 5 transmits a recipe to the vaccine manufacturing institution system 4 in a case where the recipe is received from the creation institution.

The management method according to the present embodiment further includes a step of writing an update history and/or update data of the storage 53 in a blockchain.

Note that there may be a plurality of candidates for the analysis institution and/or candidates for the creation institution and/or candidates for the manufacturing institution, and in this case, in the determination step, the delivery date management means 561 may determine a predicted delivery date or a predicted required time when the administration item is delivered to a hospital according to an analysis institution of an order destination and/or a creation institution of an order destination and/or a manufacturing institution of an order destination.

Modification 1

Next, Modification 1 of the data management method will be described. In Modification 1, in a case where the management system 5 receives the specimen ID from the hospital system 1, the management system 5 assigns the common ID, and the hospital and each institution manage data with the common ID.

FIG. 10 is a diagram illustrating a schematic configuration of a database of each system in Modification 1. As illustrated in FIG. 10, the table T5b of the management system stores records of a set of a hospital ID for identifying a hospital, a patient ID for identifying a patient, a specimen ID for identifying a specimen, a common ID for managing data, a sequence file name which is a name of a sequence file storing a gene sequence sequenced from the specimen of the patient, and a recipe file name which is a name of a recipe file storing a vaccine recipe. Here, similarly in Modification 1, the sequence file is stored, for example, in a predetermined directory for the sequence file.

Similarly in Modification 1, the specimen ID may be given to a normal tissue or blood of a patient, or may be given to a cancer tissue of a patient. Here, as an example, the specimen ID given to the normal tissue or blood of the patient and the specimen ID given to the cancer tissue of the patient are different only at the last end.

Similarly in Modification 1, the sequence file includes a file storing a sequence of DNA of a normal tissue (also referred to as normal DNA), a file storing a sequence of DNA of a cancer tissue (also referred to as cancer DNA), and a file storing a sequence of RNA of a cancer tissue (also referred to as cancer RNA). Each sequence file name is stored in the table T5b, and each sequence file is stored in the storage 53.

The table T1b of the hospital system in Modification 1 is different from the table T1 of the hospital system in FIG. 3 in that the common ID is stored instead of the vaccine ID. Here, for example, in a case of being notified from the management system 5, the common ID is stored in the table T1b by the hospital system 1.

The table T2b of the genetic analysis institution system in Modification 1 is different from the table T2 of the genetic analysis institution system in FIG. 3 in that the common ID is further stored. Here, for example, in a case of being notified from the management system 5, the common ID is stored in the table T2b by the genetic analysis institution system.

The table T3b of the recipe creation institution system 3 in Modification 1 is different from the table T3 of the recipe creation institution system 3 in FIG. 3 in that the common ID is stored instead of the recipe ID. Here, for example, in a case of being notified from the management system 5, the common ID is stored in the table T3b by the recipe creation institution system 3.

The table T4b of the vaccine manufacturing institution system 4 in Modification 1 is different from the table T4 of the vaccine manufacturing institution system 4 in that the common ID is stored instead of the vaccine ID. Here, for example, in a case of being notified from the management system 5, the common ID is stored in the table T4b by the vaccine manufacturing institution system 4.

Figure 11:
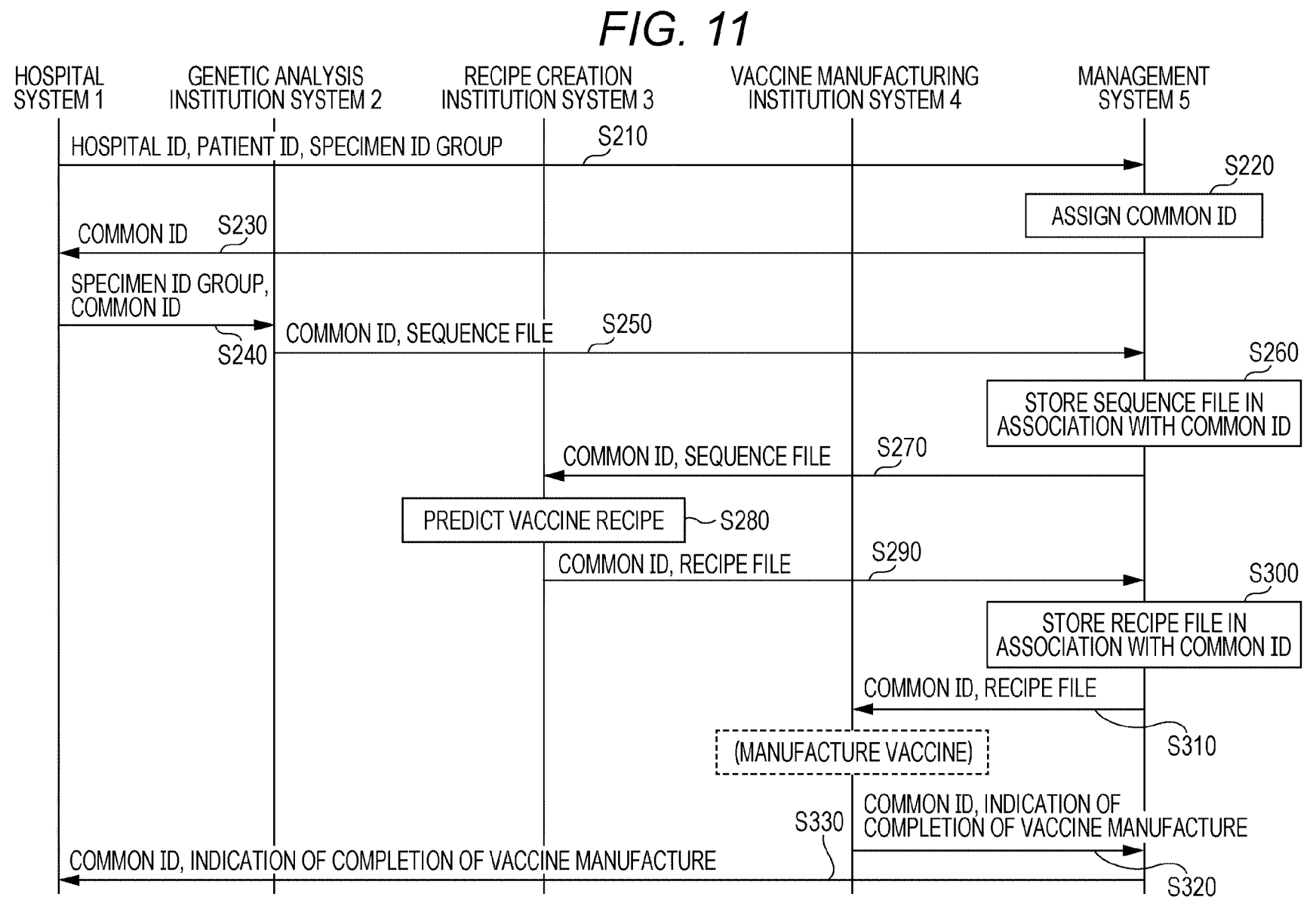

FIG. 11 is an example of a sequence diagram according to Modification 1. Hereinafter, the process of the processor of each system will be described, and the processor is not explicitly described from the viewpoint of readability.

(Step S210) First, the hospital system 1 assigns a patient ID for identifying a target patient and a specimen ID group for identifying a specimen group (for example, normal tissue or blood and cancer tissue) of the target patient, and stores them as a new record in a table T1*b* (see FIG. 10) of the hospital system 1. Here, as an example, it is assumed that the high-order four digits of the specimen ID are not the same as other specimen IDs. Furthermore, the hospital system 1 transmits, to the management system 5, for example, a set of the hospital ID for identifying the hospital (or the hospital system 1), the patient ID and the specimen ID group.

(Step S220) In a case where the management system 5 receives the set of the hospital ID, the patient ID, and the specimen ID group, the management system 5 assigns a common ID that is not the same as other common IDs, associates the common ID with the received set of the hospital ID, the patient ID, and the specimen ID, and stores the common ID as a new record in the table T5*b* (see FIG. 10) of the management system 5.

(Step S230) Next, the management system 5 notifies the hospital system 1 of the assigned common ID. In a case of where the hospital system 1 receives the common ID, the hospital system 1 updates the common ID of the record including the patient ID and the specimen ID group transmitted in step S210 with the received common ID in the table 1*b*.

(Step S240) Compared to step S30 in FIG. 4, the difference is that the hospital system 1 transmits the common ID received in step S230 to the genetic analysis institution system 2 in addition to the specimen ID group transmitted in step S210. At the same time, the hospital side sends the specimen identified by the specimen ID (for example, normal tissue or blood and cancer tissue) to the genetic analysis institution.

The specimen ID and the common ID are not limited to be transmitted by communication, and the specimen ID and the common ID may be stored in a nonvolatile memory (for example, a flash memory) and sent together with the specimen.

(Step S250) In a case of accepting the specimen ID, the common ID, and the specimen, the genetic analysis institution executes a gene sequence on the specimen and generates a sequence file storing the gene sequence. Here, as an example, a naming rule is defined in such a manner that the sequence file name is not the same as other sequence file names. For example, the sequence file name includes the high-order four digits of the specimen ID. As a result, since the high-order four digits of the specimen ID are not the same as other specimen IDs, it is possible to avoid overlapping of sequence file names.

Compared to step S40 in FIG. 4, the difference is that the genetic analysis institution system 2 stores a new set of records in table T2*b* that includes the common ID in addition to the sequence file name of the specimen ID. Compared to step S40 in FIG. 4, the difference is that the genetic analysis institution system 2 transmits the common ID, not the specimen ID, to the management system 5 in addition to the sequence file.

(Step S260) In a case where the management system 5 receives the sequence file and the common ID, the management system 5 searches a record from the table T5*b* of the management system 5 using the received common ID as a key, and updates the sequence file name of the record with the name of the received sequence file. In addition, the management system 5 stores the sequence file in a predetermined directory for the sequence file.

(Step S270) Compared to step S60 in FIG. 4, the difference is that the management system 5, for example, transmits the received common ID to the recipe creation institution system 3 in addition to the generated sequence file. The recipe creation institution system 3 receives the sequence file and the common ID.

(Step S280) In a case where the recipe creation institution system 3 receives the sequence file and the common ID, the recipe creation institution system 3 predicts the vaccine recipe using the gene sequence stored in the sequence file. Specifically, for example, the recipe creation institution system 3 predicts a peptide sequence. The recipe creation institution system 3 stores the vaccine recipe obtained from the prediction in a recipe file. Here, as an example, a naming rule is defined in such a manner that the recipe file name is not the same as other recipe file names.

(Step S290) Compared to step S80 in FIG. 3, the difference is that the recipe creation institution system 3 stores a set of the file name of the sequence file received in step S270, the recipe file generated in step S280, and the common ID received in step S270, not the recipe ID, as a new record in the table T3*b* of the recipe creation institution system. Here, as an example, a naming rule is defined in such a manner that the recipe file name is not the same as other recipe file names.

Compared to step S80 in FIG. 3, the difference is that the recipe creation institution system 3 transmits the common ID, not the recipe ID or sequence file name, to the management system 5 in addition to the recipe file generated in step S280.

(Step S300) In a case where the management system 5 receives the information transmitted in step S290, the management system 5 extracts a record in the table T5*b* using the common ID as a key, and updates the recipe file name of the record with the received recipe file name. In this manner, the management system 5 stores the recipe file in association with the common ID. In addition, the management system 5 stores the recipe file in a directory determined in advance for the recipe file.

(Step S310) Compared to step S100 in FIG. 3, the difference is that the management system 5 transmits the common ID to the vaccine manufacturing institution system 4 in addition to the received recipe file. In a case where the vaccine manufacturing institution system 4 receives the recipe file and the common ID, the vaccine manufacturing institution manufactures a vaccine based on the recipe stored in the recipe file.

(Step S320) The vaccine manufacturing institution system 4 transmits the common ID and the indication of the completion of vaccine manufacture to the management system 5.

(Step S330) In the case where the management system 5 receives the common ID and the indication of the completion of vaccine manufacture, the management system 5 notifies the hospital system 1 of the common ID and the indication of the completion of vaccine manufacture to the hospital system.

<Modification 2>

Next, Modification 2 of the data management method will be described. In Modification 2, in a case where the management system 5 receives the hospital ID, the specimen ID group, and the sequence file from the genetic analysis institution system 2, the management system 5 assigns the common ID and stores the common ID and the received specimen ID group in association with each other, the patient ID is closed in the hospital system 1 and is not transmitted to the outside, the genetic analysis institution system 2 manages data with the specimen ID, the recipe creation institution system 3 manages data with the recipe ID, and the vaccine manufacturing institution system 4 manages data with the vaccine ID.

FIG. 10 is a diagram illustrating a schematic configuration of a database of each system in Modification 2. The table T5c of the management system is obtained by deleting a column of the patient ID from the record as compared with the table T5 of the management system in FIG. 3. Here, as in FIG. 3, the sequence file is stored, for example, in a predetermined directory for the sequence file. In addition, the recipe file is stored, for example, in a predetermined directory for the recipe file.

Similarly to FIG. 3, the sequence file includes a file storing a sequence of DNA of a normal tissue (also referred to as normal DNA), a file storing a sequence of DNA of a cancer tissue (also referred to as cancer DNA), and a file storing a sequence of RNA of a cancer tissue (also referred to as cancer RNA). Each sequence file name is stored in the table T5c, and each sequence file is stored in the storage 53.

Similarly to the table T1 of the hospital system in FIG. 3, the table T1c of the hospital system stores a record of a set of the patient ID, the specimen ID, and the vaccine ID. Here, for example, when notified from the management system 5, the vaccine ID is stored in the table T1.

The table T2c of the genetic analysis institution system 2 is obtained by adding a column of the hospital ID as compared with the table T2 of the genetic analysis institution system 2 in FIG. 3. Similarly to FIG. 3, the sequence file is stored, for example, in a predetermined directory for the sequence file.

Similarly to the table T3 of the recipe creation institution system 3 in FIG. 3, the table T3c of the recipe creation institution system 3 stores a record of a set of the sequence file name which is a name of the sequence file, and the recipe ID, and the recipe file name which is a name of a recipe file. Here, as in FIG. 3, the sequence file is stored, for example, in a predetermined directory for the sequence file, and the recipe file is stored, for example, in a predetermined directory for the recipe file.

Similarly to the table T4 of the vaccine manufacturing institution system 4 in FIG. 3, the table T4c of the vaccine manufacturing institution system 4 stores a record of a set of the recipe file name which is a name of the recipe file and the vaccine ID. Here, as in FIG. 3, the recipe file is stored, for example, in a predetermined directory for the recipe file.

Figure 13:
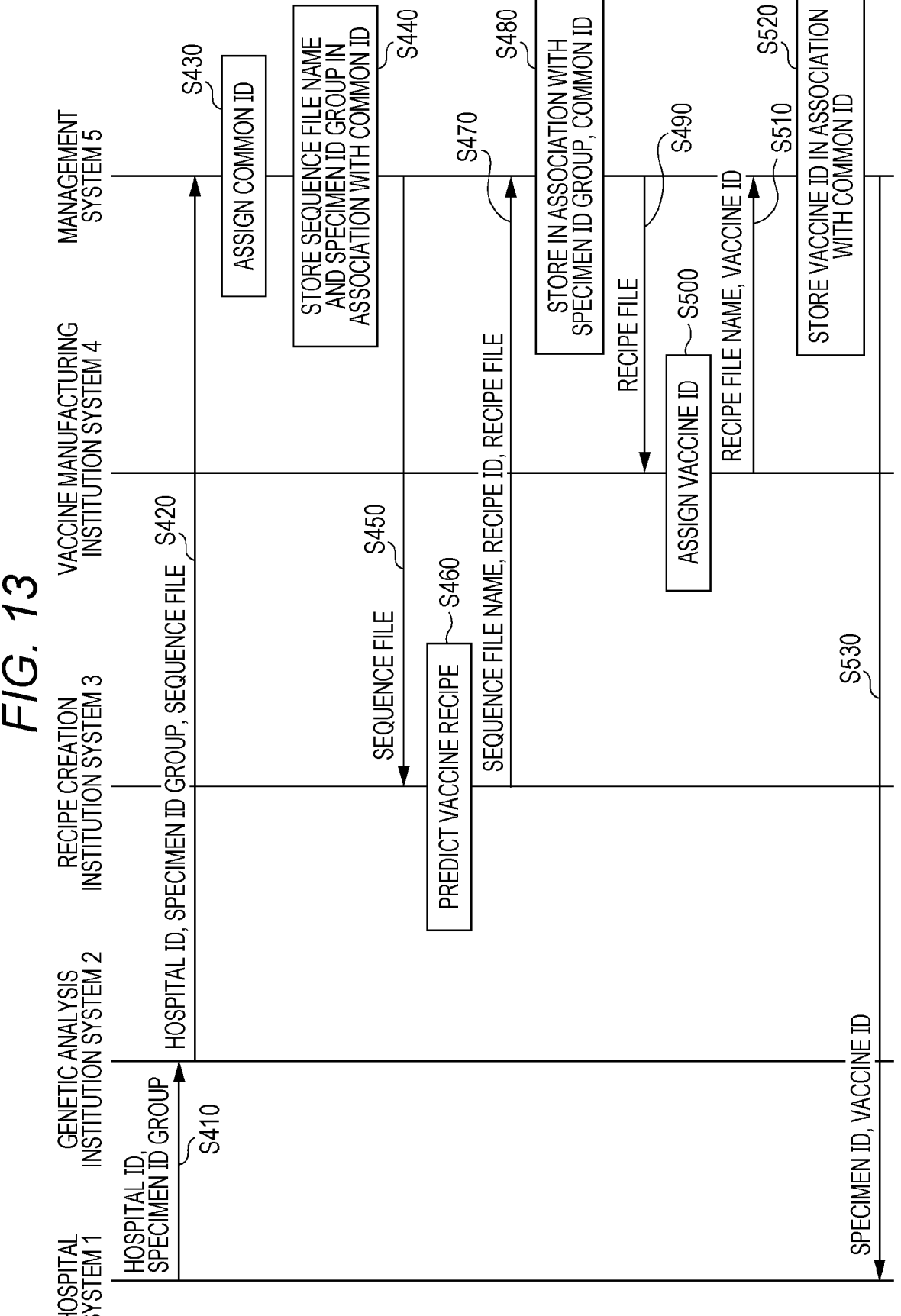
FIG. 13 is an example of a sequence diagram according to Modification 2.

FIG. 13 is an example of a sequence diagram according to Modification 2. Hereinafter, the process of the processor of each system will be described, and the processor is not explicitly described from the viewpoint of readability.

(Step S410) First, the hospital system 1 transmits the hospital ID and the specimen ID group assigned to the target specimen group to the genetic analysis institution system 2. At the same time, the hospital side sends the target specimen (for example, normal tissue or blood and cancer tissue) to the genetic analysis institution.

The hospital ID and the specimen ID group are not limited to be transmitted by communication, and the specimen ID may be stored in a nonvolatile memory (for example, a flash memory) and sent together with the specimen.

(Step S420) In a case of accepting the hospital ID and the specimen ID and the specimen, the genetic analysis institution executes a gene sequence on the specimen, generates a sequence file storing the gene sequence, and stores the sequence file in a predetermined directory for the sequence file. Here, as an example, a naming rule is defined in such a manner that the sequence file name is not the same as other sequence file names. For example, the sequence file name includes the high-order four digits of the specimen ID. As a result, since the high-order four digits of the specimen ID are not the same as other specimen IDs, it is possible to avoid overlapping of sequence file names. The genetic analysis institution system 2 stores a new record of a set of the hospital ID, the specimen ID, and the sequence file name in the table T2c.

The genetic analysis institution system 2 transmits the hospital ID to the management system 5 in addition to the sequence file and the specimen ID group.

(Step S430) In a case where the management system 5 receives the sequence file, the specimen ID group, and the hospital ID, the management system 5 assigns the common ID.

(Step S440) Then, the management system 5 adds a new record including the received specimen ID group, the received file name of the sequence file, and the assigned common ID to the table T5c of the management system 5. In this manner, the management system 5 stores the received specimen ID group and the received file name of the sequence file in association with the assigned common ID. In addition, the management system 5 stores the sequence file in a predetermined directory for the sequence file.

(Step S450) Similarly to step S60 in FIG. 4, the management system 5 transmits the sequence file to the recipe creation institution system 3, for example. The recipe creation institution system 3 receives the sequence file.

(Step S460) Similarly to step S70 in FIG. 4, in a case where the recipe creation institution system 3 receives the sequence file, the recipe creation institution system 3 predicts the vaccine recipe using the gene sequence stored in the sequence file. Specifically, for example, the recipe creation institution system 3 predicts a peptide sequence. The recipe creation institution system 3 stores the vaccine recipe obtained from the prediction in a recipe file. Here, as an example, a naming rule is defined in such a manner that the recipe file name is not the same as other recipe file names.

(Step S470) Similar to step S80 in FIG. 4, the recipe creation institution system 3 assigns a recipe ID that is not the same as other recipe IDs, and stores a set of the file name of the sequence file received in step S450, the recipe ID, and the recipe file generated in step S460 as a new record in the table T3 of the recipe creation institution system. Then, recipe creation institution system 3 transmits the set of the file name of the sequence file, the recipe ID, and the recipe file to the management system 5.

(Step S480) Similarly to step S90 in FIG. 4, in a case where the management system 5 receives the information transmitted in step S470, the management system 5 extracts a record using the received sequence file name as a key in the table T5c, and updates the recipe ID and the recipe file name of the record with the received recipe ID and the received file name of the recipe file. In this manner, the management system 5 stores the recipe ID and the recipe file name in association with the sequence file name. In addition, the management system 5 stores the recipe file in a directory determined in advance for the recipe file.

(Step S490) Similarly to step S100 in FIG. 4, the management system 5 transmits the received recipe file to the vaccine manufacturing institution system 4.

(Step S500) Similarly to step S110 in FIG. 4, in a case where the vaccine manufacturing institution system 4 receives the recipe file, the vaccine manufacturing institution manufactures a vaccine based on the recipe stored in the recipe file. Then, the vaccine manufacturing institution system 4 assigns a vaccine ID to the manufactured vaccine.

(Step S510) Similarly to step S120 in FIG. 4, the vaccine manufacturing institution system 4 transmits a set of the recipe file name of the received recipe file and the vaccine ID assigned in step S500 to the management system 5. Note that the recipe file itself may be transmitted instead of the recipe file name. In addition, the vaccine manufacturing institution system 4 adds a record of a set of the recipe file name and the vaccine ID to the table T4c (see FIG. 12) of the vaccine manufacturing institution system.

(Step S520) Similarly to step S130 in FIG. 4, the management system 5 receives the set of the recipe file name and the vaccine ID. Then, the management system 5 searches the record of the table T5c of the management system using the received recipe file name as a key, and updates the vaccine ID of the record obtained from the search with the received vaccine ID. In this way, the management system 5 stores the received vaccine ID in association with the received recipe file name.

(Step S530) Similarly to step S140 in FIG. 4, the management system 5 reads the specimen ID and the hospital ID stored in the same record as the received vaccine ID in the table T5c of the management system, and transmits the vaccine ID and the read specimen ID (or specimen ID group) to the hospital system 1 identified by the hospital ID. The hospital system 1 receives the set of the vaccine ID and the specimen ID, searches the table T1c of the hospital system using the specimen ID as a key, and updates the vaccine ID of the record obtained from the search with the received vaccine ID.

Figure 14:
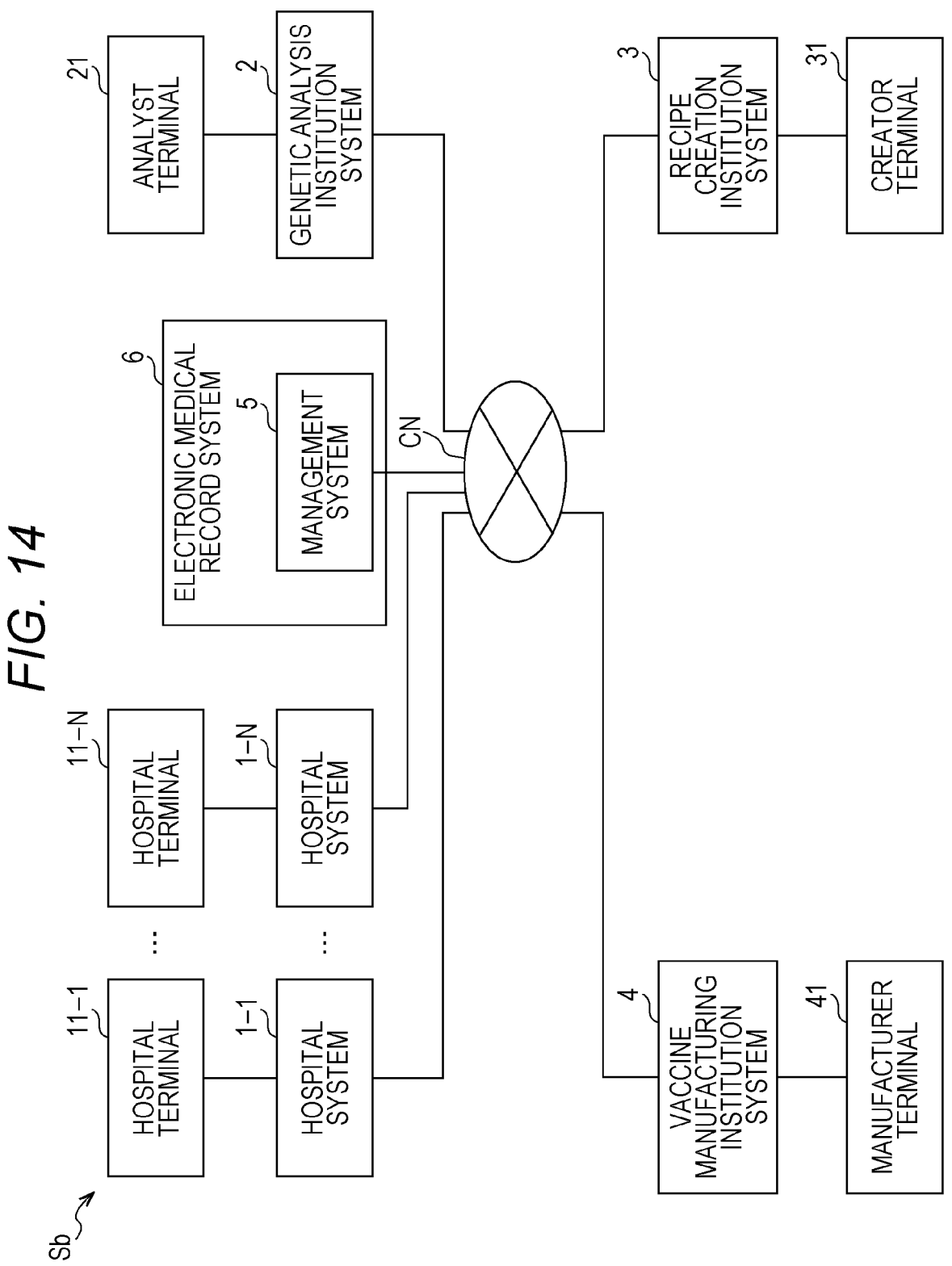
FIG. 14 is a schematic block diagram of an information processing system according to a modification of the present embodiment.

Note that, as illustrated in FIG. 14, the electronic medical record system 6 may include the management system 5. FIG. 14 is a schematic block diagram of an information processing system according to a modification of the present embodiment. As illustrated in the information processing system Sb of FIG. 14, the management system 5 may be incorporated in a part of the electronic medical record system 6.

Note that at least a part of the management system 5 described in the above-described embodiment may be configured by hardware or software. In the case of being configured by software, a program for realizing at least some functions of the management system 5 may be stored in a computer-readable recording medium and read and executed by a computer. The recording medium is not limited to a removable recording medium such as a magnetic disk or an optical disk, and may be a fixed recording medium such as a hard disk device or a memory.

In addition, a program for realizing at least some functions of the management system 5 may be distributed via a communication line (including wireless communication) such as the Internet. Further, the program may be distributed via a wired line or a wireless line such as the Internet or stored in a recording medium in an encrypted, modulated, or compressed state.

Furthermore, the management system 5 may be caused to function by one or a plurality of information devices. In the case of using a plurality of information devices, one of the information devices may be a computer, and the computer may execute a predetermined program to realize a function as at least one unit of the management system 5.

In the invention of the method, all the processes (steps) may be realized by automatic control by a computer. In addition, while causing a computer to perform each step, progress control between the steps may be performed manually. Furthermore, at least a part of all steps may be performed manually.

As described above, the present invention is not limited to the above-described embodiments as they are, and can be embodied by modifying the components without departing from the gist of the present invention in the implementation stage. In addition, various inventions can be formed by appropriately combining a plurality of constituent elements disclosed in the above embodiment. For example, some components may be deleted from all the components shown in the embodiments. Furthermore, components in different embodiments may be appropriately combined.

REFERENCE SIGNS LIST

1 Hospital system
2 Genetic analysis institution system
3 Recipe creation institution system
4 Vaccine manufacturing institution system
5 Management system
6 Electronic medical record system
51 Input interface
52 Communication module
53 Storage
54 Memory
55 Output interface
56 Processor
561 Delivery date management means
562 Communication control means
563 ID management means
564 Pipeline management means
565 Genome information management means
566 Quality information management means
S, Sb Information processing system

The invention claimed is:

1. A management method of a hospital system and executed by a server comprising at least one processor, a memory, and a network interface, the management method comprising:

receiving, via the network interface and from a system of a genetic analysis institution, a specimen identifier (ID) and a gene sequence file associated with the specimen ID, the gene sequence file named according to a collision-avoidant naming rule that deterministically encodes high-order digits of the specimen ID, the specimen ID being an identifier of a specimen obtained from a patient;

searching, by using the specimen ID as a first key, a record stored in the server;

updating, in the record, a gene sequence file name with a name of the gene sequence file received via the network interface and from the system of the genetic analysis institution;

storing, in the memory and together with the specimen ID, gene sequence data associated with the gene sequence file;

determining an estimated time, for a creation of a vaccine recipe by a recipe creation institution separate from the genetic analysis institution, by inputting at least one of a gene fragment amount of a gene to be read, a base amount of the gene to be read, a sequence data amount, and a genetic mutation amount to a machine learning model, trained using learning data, by which an estimated delivery date and the at least one of the gene fragment amount of the gene to be read, the base amount of the gene to be read, the sequence data amount, and the genetic mutation amount is output;

determining at least one of a delivery date and a required time, when an administration item is delivered to a hospital, by using an actual required time, taken by the genetic analysis institution to analyze the gene sequence data, and the estimated time for the creation of the vaccine recipe by the recipe creation institution separate from the genetic analysis institution; and transmitting, to a terminal of an authorized institution, display data, of the at least one of the delivery date and the required time, while restricting access according to institution-specific permissions;

receiving, via the network interface and from the system of the genetic analysis institution, a vaccine recipe ID, the gene sequence file name, and a vaccine recipe file, the vaccine recipe ID being assigned to the vaccine recipe file, and the vaccine recipe file being generated based on the gene sequence file associated with the specimen ID;

extracting, by using the gene sequence file name as a second key, the record and further updating, in the record and based on receiving the vaccine recipe ID, the gene sequence file name, and the vaccine recipe file, the record to indicate, in association with the gene sequence file and the gene sequence file name, the vaccine recipe ID and a name of the vaccine recipe file;

storing, in the memory, the vaccine recipe file together with the vaccine recipe ID;

updating, to an updated at least one of the delivery date and the required time, the at least one of the delivery date and the required time based on an actual required time taken by the recipe creation institution to analyze the vaccine recipe;

transmitting, to the terminal of the authorized institution, updated display data, of the updated at least one of the delivery date and the required time, while restricting access according to the institution-specific permissions; and writing, to a blockchain shared among systems of the hospital system, the genetic analysis institution, the recipe creation institution, and a manufacturing institution, a history including the at least one of the delivery date and the required time, the updated at least one of the delivery date and the required time, a set of the gene sequence data, and the specimen ID.

2. The management method according to claim 1, further comprising:

receiving, via the network interface and from the system of the genetic analysis institution, a second specimen ID and a second gene sequence file associated with the specimen ID, the second gene sequence file named according to the collision-avoidant naming rule, the second specimen ID being a second identifier of a second specimen obtained from a second patient:

searching, by using the second specimen ID as a third key, a second record stored in the server;

updating, in the second record, a second gene sequence file name with a second name of the second gene sequence file received via the network interface and from the system of the genetic analysis institution;

storing, in the memory and together with the second specimen ID, second gene sequence data associated with the second gene sequence file;

determining a second estimated time, for a second creation of a second vaccine recipe by the recipe creation institution, by inputting at least one of a second gene fragment amount of a second gene to be read, a second base amount of the second gene to be read, a second sequence data amount, and a second genetic mutation amount to the machine learning model and by which a second estimated delivery date and the at least one of the second gene fragment amount of the second gene to be read, the second base amount of the gene to be read, the second sequence data amount, and the second genetic mutation amount is output;

determining at least one of a second delivery date and a second required time, when a second administration item is delivered to the hospital, by using a second actual required time, taken by the genetic analysis institution to analyze the second gene sequence data, and the estimated time for the second creation of the second vaccine recipe by the recipe creation institution; and transmitting, to the terminal of the authorized institution, second display data, of the at least one of the second delivery date and the second required time, while restricting access according to the institution-specific permissions;

receiving, via the network interface and from the system of the genetic analysis institution, a second vaccine recipe ID, the second gene sequence file name, and a second vaccine recipe file, the second vaccine recipe ID being assigned to the second vaccine recipe file, and the second vaccine recipe file being generated based on the second gene sequence file associated with the second specimen ID;

extracting, by using the second gene sequence file name as a fourth key, the second record and further updating, in the second record and based on receiving the second vaccine recipe ID, the second gene sequence file name, and the second vaccine recipe file, the second record to indicate, in association with the second gene sequence file and the second gene sequence file name, the second vaccine recipe ID and a second name of the second vaccine recipe file;

storing, in the memory, the second vaccine recipe file together with the second vaccine recipe ID;

updating, to a second updated at least one of the second delivery date and the second required time, the at least one of the second delivery date and the second required time based on a second actual required time taken by the recipe creation institution to analyze the vaccine recipe;

transmitting, to the terminal of the authorized institution, updated display data, of the updated at least one of the delivery date and the required time, while restricting access according to the institution-specific permissions; and writing, to the blockchain shared among systems of the hospital system, the genetic analysis institution, the recipe creation institution, and the manufacturing institution, a second history indicating the second at least one of the second delivery date and the second required time, the second updated at least one of the second delivery date and the second required time, a second set of the second gene sequence data, and the second specimen ID.

3. The management method according to claim 1, wherein transmitting, to the terminal of the authorized institution, any of the display data and the updated display data, is in response to a request for a progress status from the authorized institution.

4. The management method according to claim 3,
wherein transmitting, to the terminal of the authorized institution, the any of the display data and the updated display data, is both in response to the request for the progress status from the authorized institution and is based on confirming that transmitting, to the terminal of the authorized institution, the any of the display data and the updated display data conforms with the institution-specific permissions.

5. The management method according to claim 1, further comprising:
providing, based on determining a delay to any of the at least one of the delivery date and the required time and the updated at least one of the delivery date and the required time, a notification to any of a hospital terminal of the hospital system and a doctor terminal of a doctor of the hospital system and in charge of the patient.

6. The management method according to claim 1, further comprising:
allowing a reception of setting an administration schedule to the patient based on determining that a certainty factor of the delivery date exceeds a reference.

7. The management method according to claim 1, further comprising:
transmitting the gene sequence data to the recipe creation institution based on receiving the gene sequence data from the genetic analysis institution; and
transmitting the vaccine recipe to the manufacturing institution based on receiving the vaccine recipe from the recipe creation institution.

8. The management method according to claim 1, further comprising:
storing, in the record, quality information indicating a quality of at least one of a gene sequence and the vaccine recipe.

9. The management method according to claim 8, wherein the vaccine recipe indicates at least one of peptide sequence data of neoantigens, data of proteins, and aggregate data of administered compounds.

10. The management method according to claim 1,
wherein the estimated time, for the creation of the vaccine recipe by the recipe creation institution, is based on the sequence data amount, the sequence data amount being the at least one of the gene fragment amount, the base amount, the sequence data amount, and the genetic mutation amount input to the machine learning model.

11. The management method according to claim 1,
wherein the estimated time, the creation of the vaccine recipe by the recipe creation institution, is based on the genetic mutation amount, the sequence data amount being the at least one of the gene fragment amount, the base amount, the sequence data amount, and the genetic mutation amount input to the machine learning model.

12. The management method according to claim 1,
wherein determining the estimated time for creating the recipe is further based on a name of an organ from which the specimen is obtained from the patient.

13. The management method according to claim 1,
wherein the institution-specific permissions indicate at least ones of different restrictions that are respective to ones of the genetic analysis institution, the recipe creation institution, and the authorized institution.

14. The management method according to claim 1, further comprising:
determining a confidence level by comparing the at least one of the delivery date and the required time with a predetermined threshold value established based on a historical actual delivery date and an actual required time for a delivery; and
based on determining that the confidence level exceeds the predetermined threshold value, permitting the hospital system access to the record and enabling the hospital system to input a patient vaccine administration date to the record.

15. A management system comprising:
a server having a network interface;
at least one memory storing instructions; and
at least one processor coupled to the at least one memory and configured to execute the instructions to:
receive, via the network interface and from a system of a genetic analysis institution, a specimen identifier (ID) and a gene sequence file associated with the specimen ID, the gene sequence file named according to a collision-avoidant naming rule that deterministically encodes high-order digits of the specimen ID, the specimen ID being an identifier of a specimen obtained from a patient;
search, by using the specimen ID as a first key, a record stored in the server;
update, in the record, a gene sequence file name with a name of the gene sequence file received via the network interface and from the system of the genetic analysis institution;
store, in the memory and together with the specimen ID, gene sequence data associated with the gene sequence file;
determine an estimated time, for a creation of a vaccine recipe by a recipe creation institution separate from the genetic analysis institution, by inputting at least one of a gene fragment amount of a gene to be read, a base amount of the gene to be read, a sequence data amount, and a genetic mutation amount to a machine learning model, trained using learning data, by which an estimated delivery date and the at least one of the gene fragment amount of the gene to be read, the base amount of the gene to be read, the sequence data amount, and the genetic mutation amount is output;
determine at least one of a delivery date and a required time, when an administration item is delivered to a hospital, by using an actual required time, taken by the genetic analysis institution to analyze the gene sequence data, and the estimated time for the creation of the vaccine recipe by the recipe creation institution separate from the genetic analysis institution; and
transmit, to a terminal of an authorized institution, display data, of the at least one of the delivery date and the required time, while restricting access according to institution-specific permissions;
receive, via the network interface and from the system of the genetic analysis institution, a vaccine recipe ID, the gene sequence file name, and a vaccine recipe file, the vaccine recipe ID being assigned to the vaccine recipe file, and the vaccine recipe file being generated based on the gene sequence file associated with the specimen ID;
extract, by using the gene sequence file name as a second key, the record and further updating, in the record and based on receiving the vaccine recipe ID, the gene sequence file name, and the vaccine recipe file, the record to indicate, in association with the gene sequence file and the gene sequence file name, the vaccine recipe ID and a name of the vaccine recipe file;

store, in the memory, the vaccine recipe file together with the vaccine recipe ID;

update, to an updated at least one of the delivery date and the required time, the at least one of the delivery date and the required time based on an actual required time taken by the recipe creation institution to analyze the vaccine recipe;

transmit, to the terminal of the authorized institution, updated display data, of the updated at least one of the delivery date and the required time, while restricting access according to the institution-specific permissions; and write, to a blockchain shared among systems of a hospital system, the genetic analysis institution, the recipe creation institution, and a manufacturing institution, a history including the at least one of the delivery date and the required time, the updated at least one of the delivery date and the required time, a set of the gene sequence data, and the specimen ID, the hospital system having the management system.

\* \* \* \* \*